United States Patent [19]

Tokitoh et al.

[11] Patent Number: 4,861,922

[45] Date of Patent: Aug. 29, 1989

[54] HYDROFORMYLATION OF 3-METHYL-3-BUTEN-1-OL AND ANALOGS THEREOF AND USE OF SUCH HYDROFORMYLATION PRODUCTS

[75] Inventors: Yasuo Tokitoh; Noriaki Yoshimura, both of Kurashiki, Japan

[73] Assignee: Kuraray Company, Ltd., Kurashiki, Japan

[21] Appl. No.: 13,535

[22] Filed: Feb. 11, 1987

Related U.S. Application Data

[62] Division of Ser. No. 710,852, Mar. 12, 1985, Pat. No. 4,663,468.

[30] Foreign Application Priority Data

| | | |
|---|---|---|
| Mar. 14, 1984 [JP] | Japan | 59-49962 |
| Mar. 29, 1984 [JP] | Japan | 59-62448 |
| Mar. 30, 1984 [JP] | Japan | 59-64201 |
| May 25, 1984 [JP] | Japan | 59-107012 |
| May 25, 1984 [JP] | Japan | 59-107013 |
| May 28, 1984 [JP] | Japan | 59-109087 |

[51] Int. Cl.$^4$ .......................................... C07C 27/00
[52] U.S. Cl. ................... 568/865; 549/415; 549/416; 549/420; 549/423; 568/862; 568/451
[58] Field of Search ............. 568/451, 865, 862; 549/416, 423, 420, 415

[56] References Cited

U.S. PATENT DOCUMENTS

| | | | |
|---|---|---|---|
| 3,966,827 | 6/1976 | Aquila et al. | 568/865 |
| 4,532,364 | 7/1985 | Fujioka et al. | 568/451 |

OTHER PUBLICATIONS

Journal of American Chemical Society, vol. 11, No. 2, 19th Jan., 1977, pp. 556–561, Washington, D.C., U.S.; A. J. Irwin et al.: "Asymmetric Syntheses via Enantiotopically Selective Horse Liver Alcohol Dehydrogenase Catalyzed Oxidations of Diols Containing a Prochiral Center", pp. 557, 560; scheme I*.

*Primary Examiner*—Nicky Chan
*Attorney, Agent, or Firm*—Oblon, Spivak, McClelland, Maier & Neustadt

[57] ABSTRACT

There is disclosed a method of hydroformylating 3-methyl-3-buten-1-ol and analogs thereof with carbon monoxide and hydrogen in the presence of a rhodium compound free from modification by a ligand containing an element belonging to the group V of the periodic table as well as a method of producing 3-methylpentane-1,5-diol and β-methyl-δ-valerolactone using such hydroformylation product.

4 Claims, 4 Drawing Sheets

HYDROFORMYLATION OF 3-METHYL-3-BUTEN-1-OL AND ANALOGS THEREOF AND USE OF SUCH HYDROFORMYLATION PRODUCTS

This is a division of application Serial No. 710,852, filed Mar. 12, 1985, now U.S. Pat. No. 4,663,468.

BACKGROUND OF THE INVENTION

1. Field of the Invention:

This invention relates to a method of hydroformylating 3-methyl-3-buten-1-ol and analogs thereof and to a method of producing further derivatives using such hydroformylation product.

2. Description of the Prior Art:

It is known that, in producing a hydroformylation product by reacting an olefin with carbon monoxide and hydrogen in the presence of a rhodium compound, a rhodium compound modified by a ligand containing an element belonging to the group V of the periodic table (for example, an organic tertiary phosphine such as triphenylphosphine) is used as said rhodium compound. In this method, the presence of such ligand contributes to improvement in stability of the rhodium-carbonyl complex in the reaction system. Therefore, this method is advantageous, among others, in that the catalyst activity can be maintained for a prolonged period of time and that the reaction can be carried out under milder conditions, namely at relatively low temperature and low pressure; hence, said method is highly useful for commercial purposes (refer to J. Falbe, "Carbon Monoxide in Organic Synthesis", Springer-Verlag, New York, 1970, pages 22–25, for instance).

It is also known that 3-methyl-3-buten-1-ol can be used as the olefin to be hydroformylated with carbon monoxide and hydrogen in the presence of a rhodium compound (e.g. U.S. Pat. Nos. 3,966,827 and 4,263,449). According to the patent specifications, a rhodium compound modified by the above-mentioned organic tertiary phosphine is either essential or recommended as the rhodium compound to be used in the hydroformylation of 3-methyl-3-buten-1-ol. In particular, U.S. Pat. No. 3,966,827 describes that the hydroformylation of 3-methyl-3-buten-1-ol in the presence of a rhodium-carbonyl complex modified by an organic tertiary phosphine gave 2-hydroxy-4-methyl-tetrahydropyran in about 75–91% yields. These patent specifications do not contain any specific description on the hydroformylation of 3-methyl-3-buten-1-ol in the presence of a rhodium compound free from modification by a ligand containing an element belonging to the group V of the periodic table, typically an organic tertiary phosphine.

The hydroformylation of 3-methyl-3-buten-1-ol in the presence of a rhodium compound modified by a ligand containing an element belonging to the group V of the periodic table is very slow in rate of reaction as compared with the hydroformylation of α-olefins such as propylene and 1-octene in the presence of such rhodium compound. Slow reaction rates make it necessary to use expensive rhodium compounds in larger amounts and further use larger reaction apparatus and therefore the above methods are inadequate as the methods for commercial practice. U.S. Pat. No. 3,966,827 describes to the effect that the residue containing the rhodium carbonyl complex modified by an organic tertiary phosphine, which is obtained after separation of the hydroformylation product, 2-hydroxy-4-methyltetrahydropyran, from the reaction mixture by distillation, can be reused for the subsequent hydroformylation. However, rhodium-carbonyl complexes are relatively unstable against heat even in the presence of organic tertiary phosphines capable of stabilizing the same. Thus, in the step of separating high-boiling 2-hydroxy-4-methyl-tetrahydropyran from the reaction mixture by distillation, the rhodium-carbonyl complexes in such reaction mixture is partly deteriorated (see U.S. Pat. No. 4,238,419) and, further, the catalytic activity of said rhodium-carbonyl complexes lowers due to accumulation of high-boiling byproducts in the distillation residue. It is therefore very difficult, in the practice of said method, to recycle and reuse the rhodium-carbonyl complexes and the catalysts for a long period and in a stable manner. Furthermore, the separation or recovery of said rhodium-carbonyl complexes having lowered activity from the reaction system, which is required in the practice of the above method, is troublesome and hardly efficient when said rhodium-carbonyl complexes have been modified by organic tertiary phosphines.

3-Methylpentane-1,5-diol and β-methyl-δ-valerolactone are compounds very useful as raw materials in producing polyurethanes and polyesters, for instance and there is known a method of deriving these compounds from products obtained by the above-mentioned hydroformylation of 3-methyl-3-buten-1-ol.

Thus, the above-cited U.S. Pat. No. 3,966,827 and U.S. Pat. No. 4,263,449 propose that 3-methyl-pentane-1,5-diol be produced by hydrogenating the hydroformylation product from 3-methyl-3-buten-1-ol in the presence of a hydrogenation catalyst. On the other hand, β-methyl-δ-valerolactone can be produced by oxidatively dehyrogenating 3-methylpentane-1,5-diol at a temperature of 200° C. in the presence of copper chromite [Refer to Organic Syntheses, Coll. Vol. IV, 677 (1963)]. Therefore, by combining these production methods with the above-mentioned hydroformylation of 3-methyl-3-buten-1-ol, it is possible to produce 3-methylpentane-1,5-diol and β-methyl-δ-valerolactone by using 3-methyl-3-buten-1-ol, which is readily available in commercial quantities, as the starting material. However, this series of production processes still has a problem from the practical viewpoint, for example, in that the reaction rate in the preceding hydroformylation of 3-methyl-3-buten-1-ol is very slow. Furthermore, the production of β-methyl-δ-valerolactone from 3-methyl-3-buten-1-ol requires a complicated production process since independent three reaction steps, namely hydroformylation of the starting 3-methyl-3-buten-1-ol, the subsequent hydrogenation, and oxidation, are necessary.

In Bull. Chem. Soc. Japan, 35, 986 (1962), it is described that δ-valerolactone was obtained by subjecting 2-hydroxytetrahydropyran (namely δ-oxyvaleraldehyde) to continuous vapor phase reaction at 220°–230° C. in the presence of copper-zinc oxide, copper chromite or copper chromite-zinc oxide. The present inventors found that the use of 2-hydroxy-4-methyltetrahydropyran in lieu of 2-hydroxytetrahydropyran in this known reaction gives, under the same reaction conditions, β-methyl-δ-valerolactone. Therefore, by combining this reaction with the hydroformylation of 3-methyl-3-buten-1-ol, it is possible to produce β-methyl-δ-valerolactone by a two-step reaction process starting with 3-methyl-3-buten-1-ol. However, when both 3-methylpentane-1,5-diol and β-methyl-δ-valerolactone are desired to be produced from 3-methyl-3-buten-1-ol by using the process just mentioned above, it is necessary to subject the hydroformylation product from 3-methyl-3-buten-1-ol, dividedly in a desired ratio and independently, to the hydrogenation and oxidation steps, respectively. Therefore, for this purpose, three independent reaction steps, namely hydroformylation, hydrogenation and oxidation steps, are required even when the above production process is employed. Thus, there still remains unsolved a difficulty that the production process is necessarily complicated.

It is also possible to produce β-methyl-δ-valerolactone by another method, namely by reacting ethyl β,β-dimethylacrylate with carbon monoxide and hydrogen in the presence of a cobalt catalyst [Chemische Berichte, 97, 863 (1964)]. However, this method is inadequate for use for commercial purposes since the separation of the desired β-methyl-δ-valerolactone from the reaction mixture containing by-products, such as β,β-dimethyl-γ-butyrolactone, having boiling points close to that of said desired product is not easy and moreover the starting ethyl β,β-dimethylacrylate is relatively expensive.

SUMMARY OF THE INVENTION

An object of the invention is to provide an industrially advantageous method of producing hydroformylation products from 3-methyl-3-buten-1-ol or analogs thereof at fast reaction rate.

Another object of the invention is to provide a method of producing 2-hydroxy-4-methyltetrahydropyran from 3-methyl-3-buten-1-ol at fast reaction rate and in high selectivity.

A further object of the invention is to provide a method of producing 3-methylpentane-1,5-diol from hydroformylation products from 3-methyl-3-buten-1-ol or an analog thereof in high selectivity.

A still further object of the invention is to provide a method of producing β-methyl-δ-valerolactone and 3-methylpentane-1,5-diol simultaneously from 2-hydroxy-4-methyltetrahydropyran, which is obtainable by hydroformylation of 3-methyl-3-buten-1-ol.

Some of the above objects can be achieved by providing a method of producing at least one hydroformylation product selected from the group consisting of compounds represented by the general formula

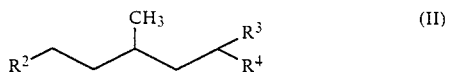

which comprises reacting a compound of the general formula

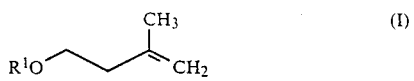

with carbon monoxide and hydrogen in the presence of a rhodium compound free from modification by a ligand containing an element belonging to the group V of the periodic table, wherein, in the above formula (I), $R^1$ is a hydrogen atom or a hydroxy-protecting group; and in the above formula (II), when $R^1$ in general formula (I) is a hydrogen atom, $R^2$ and $R^3$ in combination represent the group —O— and $R^4$ is a hydroxyl, 3-methyl-3-butenoxy, 3-methyl-5-oxopentyloxy or tetrahydro-4-methyl-2H-2-pyranoxy group and, when $R^1$ in general formula (I) is a hydroxy-protecting group, $R^2$ is the $R^1O$ group and $R^3$ and $R^4$ combinedly represent the group =O.

One of the other objects can be accomplished by providing a method of producing 3-methylpentane-1,5-diol which comprises hydrogenating the above hydroformylation product in the presence of water, a hydrogenation catalyst and an acidic substance.

One of the other objects can be attained by providing a method of simultaneously producing β-methyl-δ-valerolactone and 3-methylpentane-1,5-diol which comprises reacting one of the above hydroformylation products, namely 2-hydroxy-4-methyltetrahydropyran in a nonoxidating gas atmosphere in the presence of a specific copper-containing catalyst.

BRIEF DESCRIPTION OF THE DRAWINGS

In the accompanying drawings.

DETAILED DESCRIPTION OF THE PREFERRED EMBODIMENTS

Figure 1:
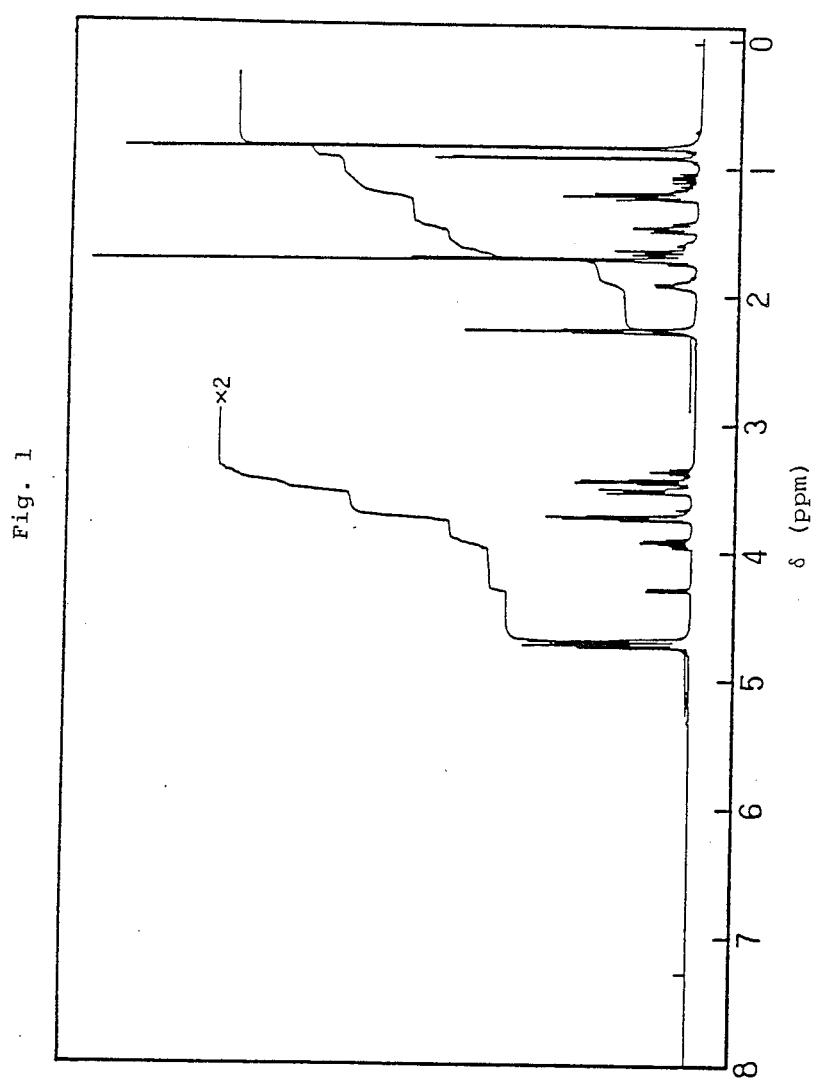
FIG. 1 is an NMR spectrum as obtained with tetrahydro-2-(3-methyl-3-butenoxy)-4-methyl-2H-pyran produced in accordance with the present invention.

The compound of general formula (I), which serves as a starting material in the practice of the invention, includes 3-methyl-3-buten-1-ol and analogs thereof respectively corresponding to the case where $R^1$ in general formula (I) is a hydrogen atom and the case where $R^1$ is a hydroxy-protecting group. As said hydroxy-protecting group, there may be used any organic protective group provided that it can substantially protect the hydroxyl group of 3-methyl-3-buten-1-ol against chemical changes in the hydroformylation reaction system (to be mentioned later) employed in accordance with the invention. Thus, said hydroxy-protecting group includes, among others, such commonly known hydroxy-protecting groups as straight or branched lower alkyl groups containing 1 to 4 carbon atoms, namely methyl, ethyl, n-propyl, isopropyl, n-butyl, isobutyl, sec-butyl and tert-butyl; aryl groups containing 6 to 8 carbon atoms, which may optionally be alkyl- or alkoxy-substituted, for example phenyl, benzyl and dimethoxyphenyl, and acyl groups containing 2 to 4 carbon atoms, for example acetyl, propionyl and butyryl. Another favorable example of the hydroxy-protecting group to be used in the practice of the invention is tetrahydro-4-methyl-2H-2-pyranyl group.

As the rhodium compound to be used in the practice of the invention, there may be used any rhodium compound capable of catalyzing the hydroformylation or being converted in the hydroformylation reaction system to thereby acquire hydroformylation-catalyzing activity, provided that it remains unmodified by a ligand containing an element belonging to the group V of the periodic table. Said element belonging to the group V of the periodic table is, for example, nitrogen, phosphorus, arsenic, or antimony. Examples of the ligand containing such element are organic tertiary phosphines such as triphenylphosphine and tributylphosphine; organic tertiary phosphites such as triphenyl phosphite and tributyl phosphite; organic tertiary arsines such as triphenylarsine and trioctylarsine; and organic tertiary stibines such as triphenylstibine. Typical examples of the rhodium compound to be used in the practice of the invention are rhodium chloride; rhodium salts of organic carboxylic acids such as rhodium acetate and rhodium propionate; rhodium-carbonyl compounds such as $Rh_4(CO)_{12}$, $Rh_6(CO)_{16}$ and $[Rh(CO)_2Cl]_2$; di-$\mu$-chlorobis(1,3-cyclopentadiene)dirhodium and di-$\mu$-chlorobis(1,5-cyclooctadiene)dirhodium. Among them particularly preferred are rhodium-carbonyl compounds, di-$\mu$-chlorobis(1,3-cyclopentadiene)dirhodium and di-$\mu$-chlorobis(1,5-cyclooctadiene)dirhodium. Metallic rhodium supported on a carrier such as activated carbon is known to form a catalytically active compound in the hydroformylation reaction system as a result of coordination bonding with carbon monoxide (cf. British Pat. No. 1,280,707, U.S. Pat. No. 3,527,809, etc.) and such metallic rhodium can also be used in the practice of the invention. The concentration of the rhodium compound in the liquid hydroformylation reaction mixture is preferably in the range of 0.005 to 5 milligram atom (as rhodium) per liter, more preferably 0.01 to 1 milligram atom (as rhodium) per liter, most preferably 0.02 to 0.5 milligram atom (as rhodium) per liter.

In accordance with the invention, the hydroformylation temperature is suitably within the range of 60° C. to 150° C., preferably 90° C. to 120° C. At temperatures below 60° C., the reaction rate is slow, whereas, at temperatures exceeding 150° C., the stability of the rhodium compound existing as the catalyst can hardly be maintained. The reaction pressure is generally within the range of 80 to 300 atmospheres (absolute), although it depends on the reaction temperature. The mole ratio between the raw material gases at the time of entering the reactor, namely the hydrogen gas/carbon monoxide gas mole ratio, is desirably within the range of about 3/1 to $\frac{1}{3}$. A gas inert to the hydroformylation reaction, such as methane, ethane, propane, nitrogen, helium, argon or carbon dioxide, may coexist in the reaction system. The hydroformylation reaction may be carried out either in the absence or in the presence of an organic solvent inert in the reaction system. Examples of such organic solvent are saturated aliphatic hydrocarbons such as propane, butane, pentane, hexane, heptane, octane, nonane, decane and octadecane; saturated alicyclic hydrocarbons such as cyclohexane, methylcyclohexane and decaline; aromatic hydrocarbons such as benzene, toluene, xylene, mesitylene, ethylbenzene and butylbenzene; ketones such as acetone, methyl ethyl ketone, methyl isobutyl ketone and cyclohexanone, ethers such as diethyl ether, diisopropyl ether, dibutyl ether, ethylene glycol dimethyl ether, diethylene glycol dimethyl ether, tetrahydrofuran and dioxane; esters such as methyl acetate, ethyl acetate, isopropyl acetate, butyl acetate, 2-ethylhexyl acetate, methyl propionate and ethyl propionate; and alcohols such as ethanol, butanol, 3-methylbutanol and 3-methylpentane-1,5-diol. Although it depends on the kind and concentration of the rhodium compound used, the reaction time required to drive the reaction to a conversion of the starting 3-methyl-3-buten-1-ol or an analog thereof which is nearly equal to 100% is generally about 1 to 10 hours. When such conversion is lower than 100%, 3-methyl-3-buten-1-ol or an analog thereof remaining unreacted can be separated from the reaction mixture and again fed as the raw material for the hydroformylation reaction.

The rhodium compound can be recovered easily by a variety of methods if necessary. Thus, for example, water is added or not added to the reaction mixture after hydroformylation and then the pressure within the system is lowered while maintaining the reaction mixture at a temperature within the range of 40° C. to the hydroformylation reaction temperature, whereby the rhodium compound precipitates out as the metal or a compound thereof. This precipitate (metallic rhodium or the rhodium compound) can be recovered by filtration, centrifugation or the like technique. It can also be recovered in a simple and easy way by contacting the reaction mixture with an adsorbent such as activated carbon or diatomaceous earth to thereby cause adsorption of the same. The rhodium compound can also be recovered from the reaction mixture in an efficient manner by causing a metal such as aluminum, zinc, chromium, iron, copper or nickel to exist in the reaction mixture and reduce the pressure within the system in the same manner as above to thereby cause precipitation of the rhodium compound, in the form metallic rhodium or the compound thereof, on the surface of the above-mentioned metal. Furthermore, it is possible to recovery the precipitate (metallic rhodium or the rhodium compound) from the distillation residue remaining after distillation of the hydroformylation reaction mixture, for example by molecular distillation. The metallic rhodium or compound thereof thus recovered can be re-used as the catalyst for the hydroformylation reaction, if necessary after purification or treatment such as the conversion to the rhodium compound by the conventional method. On the contrary, when the hydroformylation is carried out in the presence of a rhodium compound modified by a ligand containing an element belonging to the group V of the periodic table, substantial precipitation of said compound in the reaction mixture or distillation residue does not occur even when the pressure within the system is lowered in the above manner for the purpose of recovering the inactivated rhodium compound, and therefore the above-mentioned method of separation and recovery cannot be applied and many difficulties are encountered in efficient separation and recovery of the rhodium compound. Moreover, the recovery of metallic rhodium or the compound thereof is often accompanied by loss or damage of the expensive ligand, typically triphenylphosphine.

The liquid reaction mixture after hydroformylation contains a hydroformylation product consisting of at least one compound selected from the group consisting of compounds having the above-mentioned general formula (II). When the starting material is the compound of general formula (I) in which $R^1$ is a hydrogen atom, namely 3-methyl-3-buten-1-ol, $R^2$ and $R^3$ in general formula (II) combinedly represent the group —O— and $R^4$ is a hydroxyl, 3-methyl-3-butenoxy, 3-methyl-5-oxopentyloxy or tetrahydro-4-methyl-2H-2-pyranoxy group. In such case, the compound of general formula (II) has the general formula

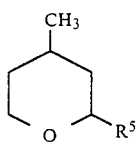

wherein $R^5$ is a hydroxyl, 3-methyl-3-butenoxy, 3-methyl-5-oxopentyloxy or tetrahydro-4-methyl-2H-2-pyranoxy group, and, specifically, is 2-hydroxy-4-methyltetrahydropyran of the formula

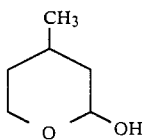

or tetrahydro-2-(3-methyl-3-butenoxy)-4-methyl-2H-pyran of the formula

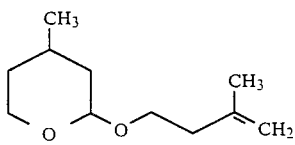

or 5-(tetrahydro-4-methyl-2H-pyranoxy)-3-methylpentanal of the formula

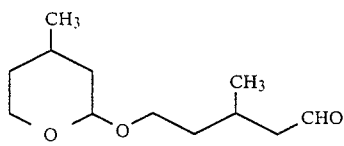

or bis(tetrahydro-4-methyl-2H-2-pyranyl) ether of the formula

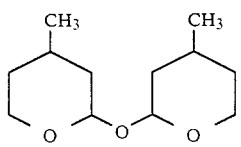

When the starting material is a compound of general formula (I) in which $R^1$ is a hydroxy-protecting group, namely an analog of 3-methyl-3-buten-1-ol, $R^2$ in general formula (II) represents the group $R^1O-$ and $R^3$ and $R^4$ in general formula (II) combinedly represent the group =O. In this case, the compound of general formula (II) is an analog of 5-hydroxy-3-methylpentanal having the general formula

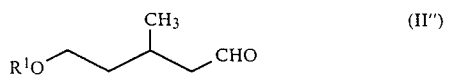

wherein $R^1$ is a hydroxy-protecting group, and is, for example, 5-acetoxy-3-methylpentanal when $R^1$ is an acethyl group, or 5-(tetrahydro-4-methyl-2H-2-pyranoxy)-3-methylpentanal when $R^1$ is a tetrahydro-4-methyl-2H-2-pyranyl group.

As mentioned above, the hydroformylation, when carried out in accordance with the present invention using 3-methyl-3-buten-1-ol as the starting material, gives a hydroformylation product consisting of at least one compound selected from compounds of general formula (II'). The above-mentioned organic solvent, when coexisting in the hydroformylation reaction system even in a small amount, increases the selectivity toward 2-hydroxy-4-methyltetrahydropyran in the hydroformylation. It has been found that, for the purpose of obtaining 2-hydroxy-4-methyltetrahydropyran as the principal hydroformylation product, it is important to cause at least one organic compound containing 3 to 18 carbon atoms, preferably 6 to 10 carbon atoms, selected from the group consisting of saturated aliphatic hydrocarbons, saturated alicyclic hydrocarbons, aromatic hydrocarbons, ketones, ethers and esters to exist in the hydroformylation reaction system as the organic solvent in an amount of not less than 10% by weight, preferably 10 to 80% by weight, more preferably 15 to 50% by weight, based on the weight of the reaction mixture. Typical examples of such organic compound containing 3 to 18 carbon atoms are saturated aliphatic hydrocarbons such as propane, butane, pentane, hexane, heptane, octane, nonane, decane and octadecane; saturated alicyclic hydrocarbons such as cyclohexane, methylcyclohexane and decalin; aromatic hydrocarbons such as benzene, toluene, xylene, mesitylene, ethylbenzene and butylbenzene; ketones such as acetone, methyl ethyl ketone, methyl isobutyl ketone and cyclohexanone; ethers such as diethyl ether, diisopropyl ether, dibutyl ether, ethylene glycol dimethyl ether, diethylene glycol dimethyl ether, tetrahydorfuran and dioxane; and esters such as methyl acetate, ethyl acetate, isopropyl acetate, butyl acetate, 2-ethylhexyl acetate, methyl propionate and ethyl propionate. These organic compounds may be used either alone or in combination of two or more. Among these particularly preferred from the viewpoints of stability in the reaction mixture and cost are saturated aliphatic hydrocarbons, saturated alicyclic hydrocarbons and aromatic hydrocarbons. To increase the amount of the organic solvent with the increase in rhodium compound concentration and/or reaction temperature generally tends to give favorable results. With the increase in the amount of such organic solvent in the reaction mixture, the selectivity toward 2-hydroxy-4-methyltetrahydropyran increases and, when said amount is not less than 10% by weight, the selectivity toward 2-hydroxy-4-methyltetrahydropyran is at a level which is practical for obtaining said compound as the objective compound. When said amount is not less than 15% by weight, said selectivity becomes markedly high. When the organic solvent is present in an amount exceeding 50% by weight, the above selectivity remains at a high level but further increase in the amount of the organic solvent generally brings about no further corresponding increase in said selectivity any more. When the organic solvent is present in an amount exceeding 80% by weight, then the reaction rate becomes slow and at the same time the volume of the organic solvent to be recovered after the hydroformylation reaction increases, which is unfavorable from the industrial viewpoint.

In carrying out the hydroformylation in the presence of an organic solvent, the conversion of 3-methyl-3-buten-1-ol is not critical. However, in some cases, driving the reaction to an extent such that the conversion of 3-methyl-3-buten-1-ol reaches almost 100% may result in conversion of 2-hydroxy-4-methyltetrahydropyran once formed to an undesired compound as a result of acetalization and so on, leading to a decrease in the selectivity toward 2-hydroxy-4-methyltetrahydropyran. When the conversion of 3-methyl-3-buten-1-ol is lower than 100%, the unreacted 3-methyl-3-buten-1-ol can be separated from the reaction mixture obtained and thereafter used for the hydroformylation reaction as the raw material. However, when the conversion of 3-methyl-3-buten-1-ol is too low, a large amount of unreacted 3-methyl-3-buten-1-ol must be separated and recovered from the liquid reaction mixture, which is not practical. Therefore, for the purpose of producing 2-hydroxy-4-methyltetrahydropyran in a particularly high selectivity and in an industrially advantageous manner, it is preferred that the conversion of 3-methyl-3-buten-1-ol is within the range of about 20 to 97%, more preferably about 50 to 95%.

The reaction mixture obtained by the hydroformylation reaction in the presence of an organic solvent contains, in addition to 2-hydroxy-4-methyltetrahydropyran, small amounts of other hydroformylation products except for the organic solvent and unreacted 3-methyl-3-buten-1-ol. After processing for the separation and recovery of the rhodium compound by the above-mentioned method as necessary, the principal product 2-hydroxy-4-methyltetrahydropyran can be separated from the liquid reaction mixture easily by subjecting the liquid reaction mixture to such separation procedure as distillation or extraction.

When 3-methyl-3-buten-1-ol is used as the starting material, the use of a specific organic solvent and specific reaction conditions and treatment conditions in the hydroformylation according to the present invention also makes it possible to separate the rhodium compound from the liquid hydroformylation reaction mixture without any substantial decrease in catalytic activity and recycle and reuse the same in the hydroformylation. It has been found that this purpose can be achieved by providing a method of producing hydroformylation products which comprises reacting 3-methyl-3-buten-1-ol with hydrogen and carbon monoxide in an organic solvent consisting essentially of a saturated aliphatic hydrocarbon and/or a saturated alicyclic hydrocarbon which may optionally contain not more than 35% by weight of an aromatic hydrocarbon in the presence of a rhodium compound free from modification by a ligand containing an element belonging to the group V of the periodic table in a concentration of 0.01 to 0.5 milligram atom (as rhodium atom) per liter at a temperature within the range of 60° to 150° C. and a pressure within the ragne of 80 to 300 atmospheres (absolute), extracting the liquid hydroformylation reaction mixture obtained with water in a mixed gas atmosphere composed of hydrogen and carbon monoxide to thereby extract the hydroformylation product into the aqueous layer to an extent such that the concentration of 2-hydroxy-4-methyltetrahydropyran in the aqueous layer amounts to not more than 2 moles/liter, and recycling the extraction residue containing the rhodium compound to the hydroformylation reaction zone.

In the production method using this extractive separation, the use, as the organic solvent in the hydroformylation reaction, of a mixed solvent composed of a saturated aliphatic hydrocarbon and/or a saturated alicyclic hydrocarbon and an aromatic hydrocarbon in which the aromatic hydrocarbon accounts for more than 35% by weight of the whole organic solvent leads to worsened separability of the extraction interface and decreased extractability in the extraction step following the reaction. The concentration of the rhodium compound in the liquid reaction mixture is required to be adjusted such that the rhodium atom concentration amounts to 0.01 to 0.5 milligram atom per liter, preferably 0.02 to 0.2 milligram atom per liter. When such concentration is lower than 0.01 milligram atom per liter, the hydroformylation reaction is slow and, when it exceeds 0.5 milligram atom per liter, the dissolution of the rhodium compound into the extractant water layer increases in the step of extraction of the liquid reaction mixture. A rhodium concentration outside the above range is thus disadvantageous from the industrial viewpoint. In the above method, an organic solvent is caused to exist in the hydroformylation reaction system, so that the selectivity toward 2-hydroxy-4-methyltetrahydropyran in the hydroformylation reaction is high and in most cases 2-hydroxy-4-methyltetrahydropyran is the principal component of said hydroformylation product. However, it is preferred that the amount of the organic solvent, the feed rate of 3-methyl-3-buten-1-ol and the residence time of the liquid reaction mixture in the reactor are selected so that the concentration of 2-hydroxy-4-methyltetrahydropyran in the liquid reaction mixture after hydroformylation can amount to about 0.5 to 5 moles per liter.

It is necessary to adjust the amount of water to be added to the liquid reaction mixture in the step of extraction of the hydroformylation product following the hydroformylation reaction such that the concentration of 2-hydroxy-4-methyltetrahydropyran in the aqueous layer after extraction is not more than 2 moles per liter, preferably 0.5 to 1.5 moles per liter. The volume of water which meets this requirement varies to some extent depending on the concentration of 2-hydroxy-4-methyltetrahydropyran in the liquid reaction mixture to be subjected to extraction, for instance, but is generally within the range of about 0.5 to 3 volumes per volume of the liquid reaction mixture to be subjected to extraction. An increased concentration of 2-hydroxy-4-methyltetrahydropyran in the extractant aqueous layer is accompanied by an increased dissolution of the rhodium compound in the aqueous layer. It is essential that the extraction procedure should be carried out in a mixed gas atmosphere composed of hydrogen and carbon monoxide so that the deposition of the rhodium compound in the liquid reaction mixture can be prevented. The hydrogen-carbon monoxide mixed gas may have the same composition as that of the raw material gas to be used in the hydroformylation reaction, and the hydrogen/carbon monoxide mole ratio is preferably within the range of about 1/3 to 3/1. The extraction procedure is preferably performed at a temperature within the range of about 0° to 50° C., more preferably about 10° to 30° C. The pressure is preferably within the range of about 1 to 300 atmospheres (absolute), more preferably about 2 to 100 atmospheres (absolute). As the extraction apparatus, there may be used, for example, an agitated-column extractor (mixer settler, rotary disc contactor, etc.) or plate column extractor (perforated plate column, etc.), which is in general and common use. In this method, the extraction residue containing the rhodium compound after the extraction step is recycled for reuse to the hydroformylation reaction zone. Part of the liquid reaction mixture after hydroformylation or of the extraction residue may be taken out for treatment, such as catalyst activation, as necessary. It is also possible to recover the rhodium compound from the liquid reaction mixture or extraction residue taken out, by the above-mentioned method of separation and recovery.

The hydroformylation product such as 2-hydroxy-4-methyltetrahydropyran can be isolated from the aqueous extract containing the hydroformylation product obtained by the above extraction procedure, by such separation technique as distillation or extraction. In particular, the hydroformylation product can be isolated efficiently by reextracting the aqueous extract containing the hydroformylation product with a specific organic extractant. Such organic extractant is a substantially water-soluble one and is selected from among esters such as isopropyl acetate, butyl acetate, isobutyl acetate, isoamyl acetate and methyl propionate; ketones such as methyl isobutyl ketone and dibutyl ketone; aromatic hydrocarbons such as benzene and toluene; and 3-methyl-3-buten-1-ol. These are used either alone or in admixture of two or more. The organic extractant is used generally in an amount of about 0.2 to 3 volumes pe volume of the aqueous solution containing the hydroformylation product. When the amount of the organic extractant is less than about 0.2 volume per volume of the aqueous solution, a fairly large amount of the hydroformylation product remains in the aqueous extraction residue solution, whereby the extraction cannot be efficient in some instances. The use of larger amount of organic extractant tends to increase the transfer of the hydroformylation product from the aqueous solution to the organic extractant but, when the amount of organic extractant exceeds about 3 volumes per volume of the aqueous solution, further increase in the amount of organic extractant will not produce further increase in the transfer of the hydroformylation product into the organic extractant any more and will result in the mere use of an unduly large amount of organic extractant. The extraction temperature is not critical but is preferably within the range of about 0° to 100° C. The atmosphere to be used in the extraction procedure is not critical unless adversely affecting the hydroformylation reaction. However, it is preferable to perform the extraction procedure in a hydrogen-carbon monoxide mixed gas or a gas inert to the hydroformylation reaction, such as methane, ethane, propane, nitrogen, helium, argon or carbon dioxide, more preferably in a hydrogen-carbon monoxide mixed gas atmosphere. As the pressure during extraction, there may be applied a pressure generally used in ordinary extraction procedures, and a pressure in the neighborhood of atmospheric pressure is in general advantageous.

The hydroformylation product such as 2-hydroxy-4-methyltetrahydropyran can be isolated by subjecting the organic layer obtained by reextraction to separation procedure such as distillation. The separation of the hydroformylation product from the organic solution by distillation requires less heat energy as compared with the separation of the hydroformylation product from an aqueous solution and therefore advantageous from the industrial viewpoint. In some instances, a small amount of hydroformylation product may remain dissolved in the extraction residue aqueous solution obtained in the reextraction. Therefore, it is preferable to recycle for reuse the extraction residue aqueous solution to the above-mentioned zone where the hydroformylation product are extracted with water.

As regards the hydroformylation of 3-methyl-3-buten-1-ol and analogs thereof, it is known in the art that 3-methyl-3-buten-1-ol can be hydroformylated in the presence of a rhodium compound modified by an organic tertiary phosphine. As compared with such prior art method, the method of the present invention according to which the hydroformylation of 3-methyl-3-buten-1-ol or analogs thereof is carried out in the presence of a rhodium compound free from modification by a ligand containing an element belonging to the group V of the periodic table gives the hydroformylation product at a much faster reaction rate. In accordance with the invention, it is also possible to separate and recover the rhodium compound used in the hydroformylation step from the hydroformylation reaction mixture in a simple and easy manner or to separate said compound from the hydroformylation reaction mixture while maintaining its catalitic activity and recycle for reuse to the hydroformylation step. In accordance with the present invention, it is further possible to obtain 2-hydroxy-4-methyltetrahydropyran at a fast reaction rate and in high selectivity by selecting the hydroformylation conditions.

The 2-hydroxy-4-methyltetrahydropyran obtained in accordance with the present invention can easily be converted to β-methyl-δ-valerolactone by dehydrogenating in the presence of an oxidative dehydrogenation catalyst such as copper chromite. Furthermore, 2-hydroxy-4-methyltetrahydropyran can be easily converted to 3-methylpentane-1,5-diol by hydrogenating in the presence of a hydrogenation catalyst such as Raney nickel, nickel-on-diatomaceous earth or copper chromite.

In accordance with the present invention, there can be obtained, as the hydroformylation product from 3-methyl-3-buten-1-ol, the following compounds, either alone or in the form of a mixture of two or more: 2-hydroxy-4-methyltetrahydropyran, tetrahydro-2-(3-methyl-3-butenoxy)-4-methyl-2H-pyran, 5-(tetrahydro-4-methyl-2H-2-pyranoxy)-3-methylpentanal and bis(tetrahydro-4-methyl-2H-2-pyranyl)ether. The components other than 2-hydroxy-4-methyltetrahydropyran can be converted to 2-hydroxy-4-methyltetrahydropyran by subjecting to hydrolysis. Accordingly, in cases where 2-hydroxy-4-methyltetrahydropyran is to be produced by hydrolyzing the hydroformylation products obtained, there is no need of isolating the respective components in the hydroformylation product in advance.

In accordance with the present invention, it is also possible to obtain, in addition to the above-mentioned compounds, various 5-hydroxy-3-methylpentanal analogs in high yields as the hydroformylation product from 3-methyl-3-buten-1-ol analogs. Such 5-hydroxy-3-methyl-pentanal analogs can be converted to 2-hydroxy-4-methyltetrahydropyran by such treatment as hydrolysis and is useful as an intermediate for the synthesis of drugs and perfumes, for instance.

The hydroformylation product obtained in accordance with the present invention can be converted to 3-methylpentane-1,5-diol in one reaction step as will be mentioned later herein.

Furthermore, the 2-hydroxy-4-methyltetrahydropyran obtained in accordance with the present invention can be used as an intermediate for the simultaneous parallel production of β-methyl-δ-valerolactone and 3-methylpentane-1,5-diol by the method to be mentioned later herein.

Production of 3-methylpentane-1,5-diol:

3-Methylpentane-1,5-diol can be produced by hydrogenating, in the presence of water, a hydrogenation catalyst and an acidic substance, the hydroformylation product obtained by the method according to the present invention from a compound of the general formula

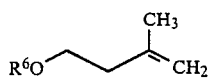
(I')

wherein $R^6$ is a hydrogen atom or a tetrahydro-4-methyl-2H-2-pyranyl group, namely 3-methyl-3-buten-1-ol or tetrahydro-2-(3-methyl-3-butenoxy)-4-methyl-2H-pyran.

The hydroformylation product to be subjected to hydrogenation is a hydroformylation product consisting of one compound or a mixture of two or more compounds selected from the group consisting of the compounds of the above formula (II') as obtained from 3-methyl-3-buten-1-ol or a hydroformylation product consisting of 5-(tetrahydro-4-methyl-2H-2-pyranoxy)-3-methylpentanal obtained from tetrahydro-2-(3-methyl-3-butenoxy)-4-methyl-2H-pyran. In carrying out the hydrogenation, such hydroformylation product can be used as it is, without isolation of each component, as the raw material for the hydrogenation reaction.

Examples of the hydrogenation catalyst, which are usable in the above hydrogenation reaction, are various hydrogenation catalysts such as Raney nickel, Raney cobalt, palladium black, copper chromite and nickel, ruthenium, cobalt, palladium or copper chromite supported on a carrier such as diatomaceous earth, alumina or carbon. Particularly preferred are nickel catalysts. These catalysts may be partly modified with chromium, molybdenum, manganese, tungsten, etc. The use of a hydrogenation catalyst treated in advance with a carboxylic acid such as acetic acid or propionic acid is very favorable from the viewpoint of the presence of an acidic substance in the hydrogenation reaction system.

As the solvent in carrying out the hydrogenation, there may be used water either alone or in combination with an optionally selected organic solvent incapable of adversely affecting the hydrogenation reaction. Preferred as said organic solvent are those organic solvents which are at least partially soluble in water, such as lower alcohols, e.g. methanol, ethanol, propanol, butanol and isoamyl alcohol; 3-methylpentane-1,5-diol; and ethers, e.g. tetrahydrofuran and dioxane. However, hydrocarbons such as hexane, cyclohexane, benzene and toluene may also be used.

Water is required to be present in the hydrogenation reaction system so that hydroformylation product compounds other than 2-hydroxy-4-methyltetrahydropyran can be hydrolyzed. The amount of water can be selected arbitrarily in not less than the stoichiometrically required amount. Whether an organic solvent is used or not, it is in general preferred that water be present in the hydrogenation reaction mixture in an amount of not less than about 0.05 part by weight, more preferably within the range of about 0.1 to 5 parts by weight, per part by weight of the hydroformylation product.

The hydrogenation is performed in the presence of an acidic substance. The term "acidic substance" as used herein includes, among others, solid acids, such as cation exchange resins, silica-alumina, silica, alumina and diatomaceous earth; organic acids, such as acetic acid, propionic acid, isovaleric acid and benzoic acid; and inorganic acids, such as phosphoric acid, boric acid, hydrochloric acid and sulfuric acid. However, organic acids are preferred. Said solid acids may also serve as the carriers for the above-mentioned hydrogenation catalysts. When the organic or inorganic acid is employed as the acidic substance, it is necessary that such organic or inorganic acid should be present in the reaction mixture in an amount sufficient to render the reaction mixture acidic, preferably in an amount sufficient to acidify the reaction mixture to a pH within the range of 1 to 5.5, more preferably 3 to 5. When the reaction mixture has a pH lower than 1, the hydrogenation catalyst decreases in catalyst activity due to partial dissolution thereof in the solution. When the pH is higher than 5.5, the rate of reaction or yield of 3-methylpentane-1,5-diol decreases. The case in which the hydrogenation of the hydroformylation product is carried out in the presence of water and a hydrogenation catalyst under acidic conditions of course fall within the scope of the above hydrogenation method. When the solid acid is employed, the solid acid concentration to be attained in the reaction mixture is generally within the range of 0.05 to 10% by weight based on the weight of the reaction mixture although said concentration depends on the acid strength of the solid acid and the number of acid sites therein. It is preferable to cause the above acidic substance, such as a solid acid, organic acid or inorganic acid, to be present in the reaction mixture from the beginning of the hydrogenation step. However, it is also possible to add said acidic substance to the reaction mixture in the course of the hydrogenation reaction.

The hydrogenation can be carried out using either a fixed bed or a suspended bed. The hydrogenation reaction temperature is generally within the range of 50° to 250° C., preferably 80° to 200° C., most preferably 70° to 150° C. The hydrogen pressure in the reaction system depends on the kind of hydrogenation catalyst employed but is generally within the range of 2 to 200 atmospheres (absolute), preferably 5 to 150 atmospheres (absolute), most preferably 10 to 100 atmospheres (absolute), for the cases where nickel catalysts, such as Raney nickel and nickel-on-diatomaceous earth; cobalt catalysts, such as Raney cobalt and cobalt-on-diatomaceous earth; and palladium catalysts, such as palladium black and palladium-on-carbon, are used as the hydrogenation catalysts, or generally within the range of 50 to 300 atmospheres (absolute), preferably 100 to 250 atmospheres (absolute), for the cases where copper catalysts, such as copper chromite, are used as the hydrogenation catalysts.

The hydrogenation product obtained by the above hydrogenation contains 3-methylpentane-1,5-diol as the main component thereof and also contains, in some instances, small amounts of by-products such as isoamyl alcohol. The desired 3-methylpentane-1,5-diol can be isolated from the reaction mixture after hydrogenation by an optionally selected separation procedure such as fractional distillation following the removal of the hydrogenation catalyst, acidic substance, water, and the solvent used (if any).

The application of this hydrogenation to the hydroformylation product from tetrahydro-2-(3-methyl-3-butenoxy)-4-methyl-2H-pyran is particularly favorable for the purpose of markedly increasing the selectivity toward 3-methylpentane-1,5-diol while inhibiting the formation of by-product isoamyl alcohol.

Tetrahydro-2-(3-methyl-3-butenoxy)-4-methyl-2H-pyran can be produced in almost quantitative yield, for example by dehydration-condensation of 2-hydroxy-4-methyltetrahydropyran with 3-methyl-3-buten-1-ol in the presence of an acid catalyst (method 1), by subjecting an 2-alkoxy-tetrahydro-4-methyl-2H-pyran of the general formula

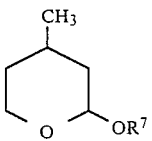

wherein R[7] is a lower alkyl group containing not more than 4 carbon atoms, and 3-methyl-3-buten-1-ol to acetal exchange in the presence of an acid catalyst (method 2), or by reacting 5-(tetrahydro-4-methyl-2H-2-pyranoxy)-3-methylpentanal with 3-methyl-3-buten-1-ol in the presence of an acid catalyst (method 3). The reaction involved in method 3 is given by the following reaction equation, 1 mole of 5-(tetrahydro-4-methyl-2H-2-pyranoxy)-3-methylpentanal yielding 2 moles of tetrahydro-2-(3-methyl-3-butenoxy)-4-methyl-2H-pyran:

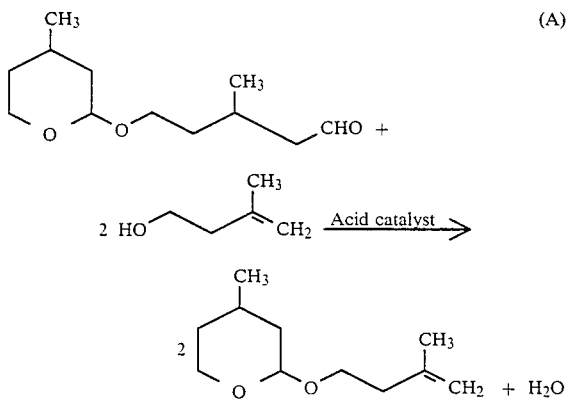

The acid catalyst to be used in the above methods 1–3 may be either a protonic acid or a Lewis acid. The protonic acid includes, among others, organic carboxylic acids such as acetic acid, propionic acid, 2-ethylhexanoic acid, benzoic acid and terephthalic acid; organic sulfonic acids such as benzenesulfonic acid and p-toluenesulfonic acid; acidic macromolecular compounds such as cation exchange resins and phenolic resins; and inorganic protonic acids such as sulfuric acid, hydrochloric acid, phosphoric acid, sodium hydrogensulfate and sodium dihydrogenphosphate, whereas the Lewis acid includes copper sulfate, nickel chloride, calcium chloride, ferric chloride, zinc chloride, alumina, silica alumina, active clay, etc. Among these, particularly preferred from the viewpoint of easy separation of the catalyst are solid acids such as cation exchange resins and silica alumina. The amount of the acid catalyst is not particularly critical but generally within the range of 0.01 to 10% by weight based on the weight of the reactant. The quantitative ratio of 2-hydroxy-4-methyltetrahydropyran, 2-alkoxytetrahydro-4-methyl-2H-pyran or 5-(tetrahydro-4-methyl-2H-2-pyranoxy)-3-methylpentanal to 3-methyl-3-buten-1-ol is preferably equal or close to the stoichiometric one. Thus, it is preferable to react about 0.7 to 1.2 moles of 2-hydroxy-4-methyltetrahydropyran (in method 1), about 0.7 to 1.2 moles of 2-alkoxy-tetrahydro-4-methyl-2H-pyran (in method 2) or about 0.4 to 0.55 mole of 5-(tetrahydro-4-methyl-2H-2-pyranoxy)-3-methylpentanal (in method 3) with one mole of 3-methyl-3-buten-1-ol. However, such quantitative ratio is not limited to the above-mentioned one. For example, 3-methyl-3-buten-1-ol may be used in excess. The reaction temperature is generally within the range of 0° to 150° C., preferably 20° to 100° C. In carrying out the above methods, it is not always necessary that a solvent be present in the reaction system. However, an optionally selected solvent may be used provided that the reaction is not adversely affected thereby. Usable solvents are saturated aliphatic hydrocarbons such as hexane, heptane and octane; saturated alicyclic hydrocarbons such as cyclohexane and methylcyclohexane; aromatic hydrocarbons such as benzene, toluene and xylene; halogenated hydrocarbons such as methylene chloride, chloroform, carbon tetrachloride and dichloroethane; ethers such as diethyl ether, tetrahydrofuran, dioxane and diethylene glycol dimethyl ether; and ketones such as acetone, methyl ethyl ketone and methyl isobutyl ketone. It is particularly preferable to use a saturated aliphatic hydrocarbon, saturated alicyclic hydrocarbon or aromatic hydrocarbon and conduct the reaction while removing water or lower alcohol, which is formed, from the reaction system. The amount of the solvent is not critical but, from the viewpoint of the solvent recovery, it is in general suitable to use not more than 20 parts by weight of solvent per part by weight of reactants.

When the above method 3 is combined with the production of 3-methylpentane-1,5-diol by hydrogenation of the hydroformylation product from tetrahydro-2-(3-methyl-3-butenoxy)-4-methyl-2H-pyran and part of 5-(tetrahydro-4-methyl-2H-2-pyranoxy)-3-methylpentanal, which is the hydroformylation product from tetrahydro-2-(3-methyl-3-butenoxy)-4-methyl-2H-pyran, is used for the production of tetrahydro-2-(3-methyl-3-butenoxy)-4-methyl-2H-pyran with the remaining portion of said hydroformylation product being directed to the production of 3-methylpentane-1,5-diol, the resulting production process involves the following three reactions:

(i) Formation of 5-(tetrahydro-4-methyl-2H-2-pyranoxy)-3-methylpentanal by the hydroformylation of tetrahydro-2-(3-methyl-3-butenoxy)-4-methyl-2H-pyran;

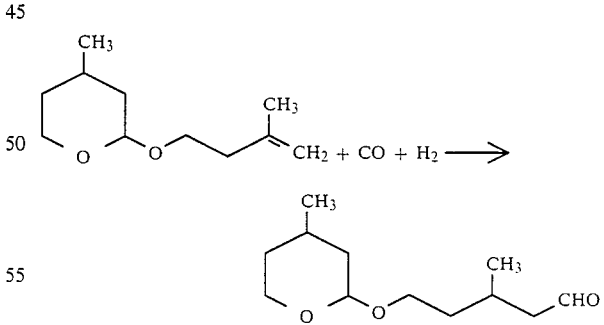

(ii) Formation of 3-methylpentane-1,5-diol by the hydrogenation of 5-(tetrahydro-4-methyl-2H-2-pyranoxy)-3-methylpentanal;

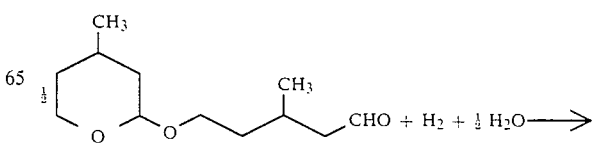

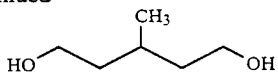
and (iii) Formation of tetrahydro-2-(3-methyl-3-butenoxy)-4-methyl-2H-pyran by the acetal exchange between 5-(tetrahydro-4-methyl-2H-2-pyranoxy)-3-methylpentanal and 3-methyl-3-buten-1-ol:

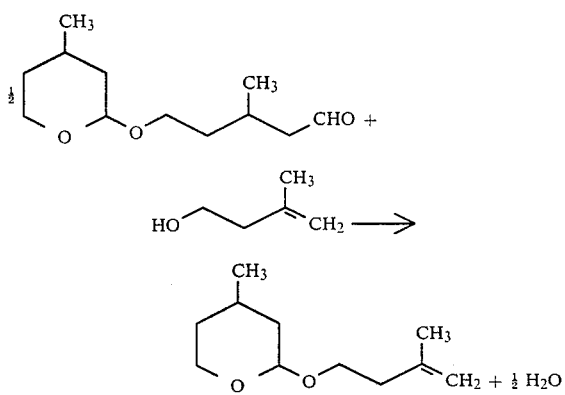

As the result of the combination of these reactions, 3-methylpentane-1,5-diol can be produced from 3-methyl-3-buten-1-ol, carbon monoxide and hydrogen, as shown by the reaction equation given below:

(i) + (ii) + (iii):

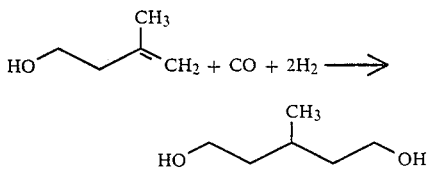

Tetrahydro-2-(3-methyl-3-butenoxy)-4-methyl-2H-pyran and 5-(tetrahydro-4-methyl-2H-2-pyranoxy)-3-methylpentanal are novel compounds which have not yet been described in the literature, and they are important intermediates in synthesizing 3-methylpentane-1,5-diol from 3-methyl-3-buten-1-ol by the above-mentioned process.

Simultaneous production of β-methyl-δ-valerolactone and 3-methylpentane-1,5-diol:

β-Methyl-δ-valerolactone and 3-methylpentane-1,5-diol can be produced simultaneously by reacting 2-hydroxy-4-methyltetrahydropyran at a temperature of 110° to 190° C. in a nonoxidizing gas atmosphere in the presence of a catalyst containing a mixed oxide of copper and at least one metal selected from the group consisting of chromium and zinc.

Said 2-hydroxy-4-methyltetrahydropyran to be used in the above simultaneous production can be produced from 3-methyl-3-buten-1-ol by the above-mentioned hydroformylation according to the present invention. Such hydroformylation is preferably carried out in the presence of an organic solvent to thereby increase the selectivity toward 2-hydroxy-4-methyltetrahydropyran, as mentioned hereinbefore. Specifically, the catalyst to be used in said simultaneous production contains copper chromite, copper-chromium oxide, copper-zinc oxide or copper-chromium-zinc oxide as the main effective catalyst component. The effective catalyst component may be used either alone as it is or in the form supported on a carrier such as alumina, silica or diatomaceous earth. Catalysts of this kind are commercially produced and readily available and, moreover, can be prepared by the methods described, for example, in Organic Synthesis, Coll. Vol. II, 142 (1943); J. Am. Chem. Soc., 54, 1138 (1932); J. Am. Chem. Soc., 58, 1053 (1936); Ind. Eng. Chem., 27, 134 (1935); and Ind. Eng. Chem., 21, 1052 (1929). The catalyst may be partly modified with other metal, such as a metal selected from tungsten, molybdenum, rhenium, zirconium, manganese, titanium, iron, barium, magnesium, calcium, etc., or a compound thereof. Some catalysts may be improved in catalytic activity by treatment with hydrogen prior to use. Such catalysts are generally used singly, although they may of course be used in combination of two or more. The reaction involved in this simultaneous production method is carried out in the liquid phase using either a suspended bed or fixed bed.

Said reaction is conducted at a reaction temperature within the range of 110° to 190° C., preferably 130° to 180° C. At a reaction temperature below 110° C., the reaction rate is slow or the reaction does not progress to a substantial extent. At a temperature higher than 190° C., the formation of 3-methylpentane-1,5-diol is inhibited, whereby it is very difficult in some cases to obtain 3-methylpentane-1,5-diol in a satisfactory yield.

The reaction for said simultaneous production is performed in a nonoxidizing gas atmosphere to thereby avoid oxidation of the raw material and of the product. Typical and preferred nonoxidizing gases are inert gases such as nitrogen, helium and argon, and hydrogen gas. These nonoxidizing gases may be used either singly or in admixture of two or more. Among them, nitrogen gas or hydrogen gas is preferably used. Since the reaction involved in this simultaneous production process can give β-methyl-δ-valerolactone and 3-methylpentane-1,5-diol simultaneously in a β-methyl-δvalerolactone/3-methylpentane-1,5-diol mole ratio of not less than 1/1 even in a nonoxidizing gas atmosphere other than hydrogen, it is assumed that 2-hydroxy-4-methyltetrahydropyran undergoes dehydrogenation on the surface of the effective catalyst component, giving β-methyl-δ-valerolactone and hydrogen and that this hydrogen then effectively reacts with 2-hydroxy-4-methyltetrahydropyran to give 3-methylpentane-1,5-diol. In a hydrogen gas atmosphere or in a mixed gas atmosphere composed of hydrogen gas and another nonoxidizing gas, the formation of 3-methylpentane-1,5-diol is further promoted and, when the reaction conditions are adequately selected, β-methyl-δ-valerolactone and 3-methylpentane-1,5-diol can be produced in a β-methyl-δ-valerolactone/3-methylpentane-1,5-diol mole ratio of not only 1/1 or more but also less than 1/1. The reaction pressure is preferably at least 0.01 atmosphere (absolute) and lower than 20 atmospheres (absolute). When the pressure is 20 atmospheres (absolute) or higher, the formation of β-methyl-δ-valerolactone is inhibited, so that, in some instances, β-methyl-δ-valerolactone can hardly be obtained in a satisfactory yield. At a pressure lower than 0.01 atmosphere (absolute), the formation of 3-methylpentane-1,5-diol is inhibited, whereby it is difficult in some instances to obtain 3-methylpentane-1,5-diol in a satisfactory yield.

Whereas, in this reaction, the starting material 2-hydroxy-4-methyltetrahydropyran and/or the products β-methyl-δ-valerolactone and 3-methylpentane-1,5-diol may serve as the solvent, it is also possible to use some other organic solvent. Any organic solvent can be used provided that it is inert to the reaction and 2-hydroxy-4-methyltetrahydropyran, β-methyl-δ-valerolactone and 3-methylpentane-1,5-diol are soluble therein. More specifically, there may be mentioned, for example, saturated aliphatic hydrocarbons, aromatic hydrocarbons, ethers and esters, such as liquid paraffin, hexane, benzene, toluene, biphenyl, diethylene glycol dimethyl ether, triethylene glycol dimethyl ether and dioctyl phthalate. In solvent selection, the intended reaction temperature and pressure as well as the boiling point difference from 2-hydroxy-4-methyltetrahydropyran, β-methyl-δ-valerolactone and 3-methylpentane-1,5-diol should of course be taken into consideration.

The reaction may be conducted either batchwise or continuously, although continuous feeding of 2-hydroxy-4-methyltetrahydropyran to the reaction zone is preferred. After catalyst separation, β-methyl-δ-valerolactone, 3-methylpentane-1,5-diol and possibly existing unreacted 2-hydroxy-4-methyltetrahydropyran can readily be isolated by a conventional procedure, for example by distillation.

According to the prior art methods, production of β-methyl-δ-valerolactone and 3-methylpentane-1,5-diol requires respective independent production facilities. On the contrary, the simultaneous production method can produce β-methyl-δ-valerolactone and 3-methylpentane-1,5-diol simultaneously from 2-hydroxy-4-methyltetrahydropyran with a common reactor and under relatively mild conditions. According to this simultaneous production thereof, β-methyl-δ-valerolactone and 3-methylpentane-1,5-diol are produced generally in a β-methyl-δ-valerolactone/3-methylpentane-1,5-diol mole ratio of about 70/30 to 15/85. Said simultaneous production method can give β-methyl-δ-valerolactone and 3-methylpentane-1,5-diol each in a satisfactory yield and in a yield ratio therebetween selected depending on the demands therefor.

Having generally described this invention, a further understanding can be obtained by reference to certain specific examples which are provided herein for purpose of illustration only and are not intended to be limiting unless otherwise specified.

EXAMPLE 1

(a) Production of tetrahydro-2-(3-methyl-3-butenoxy)-4-methyl-2H-pyran

Figure 2:
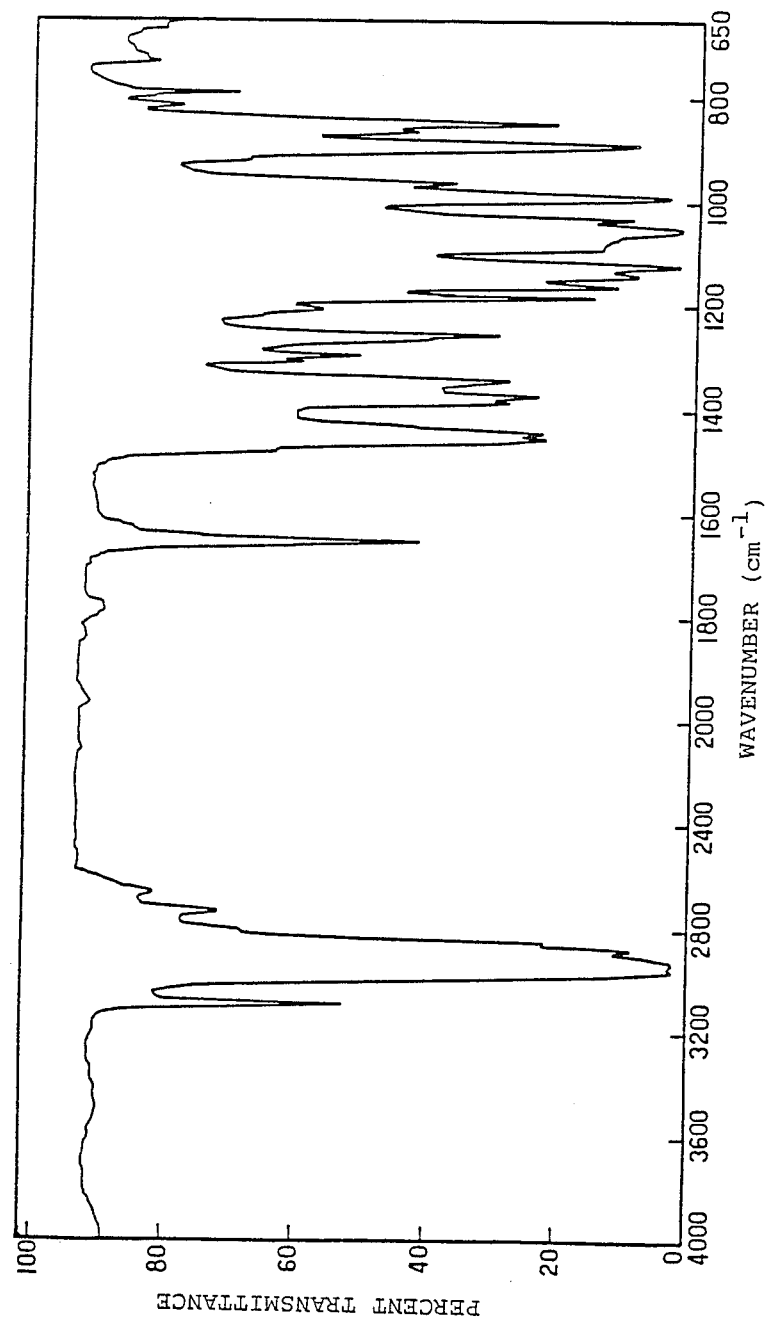
FIG. 2 is an IR spectrum as obtained with tetrahydro-2-(3-methyl-3-butenoxy)-4-methyl-2H-pyran produced in accordance with the present invention.

A 300-ml three-necked flask equipped with condensor, stirrer and thermometer was charged with 70 g (0.60 mole) of 2-hydroxy-4-methyltetrahydropgran, 52.46 g (0.61 mole) of 3-methyl-3-buten-1-ol, 150 ml of hexane and 3 g of active clay, and the mixture was stirred at 60° C. for 1 hour. Thereafter, the reaction mixture was analyzed by gas chromatography. The chromatogram showed no peak for 2-hydroxy-4-methyltetrahydropyran but showed a new peak. The active clay was filtered off from the reaction mixture, then, the hexane was distilled off and the residue was distilled under reduced pressure to give 105 g (98% yield) of tetrahydro-2-(3-methyl-3-butenoxy)-4-methyl-2H-pyran as a fraction boiling at 89.5°–90.0° C./10 mm Hg. A nuclear magnetic resonance (NMR) spectrum (in CDCl$_3$) and an infrared absorption spectrum (liquid film-NaCl method) each obtained with the above product are shown in FIG. 1 and FIG. 2, respectively. The NMR spectrum suggested this product was a mixture of 70% of

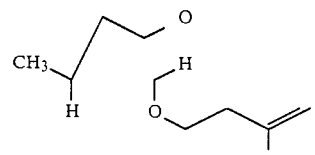

and 30% of

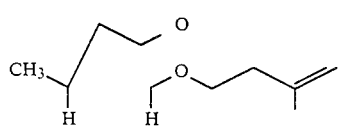

Field desorption ionization (FD) mass spectrometry of this product gave M$^+$ = 184.

(b) Hydroformylation of tetrahydro-2-(3-methyl-3-butenoxy)-4-methyl-2H-pyran

Figure 3:
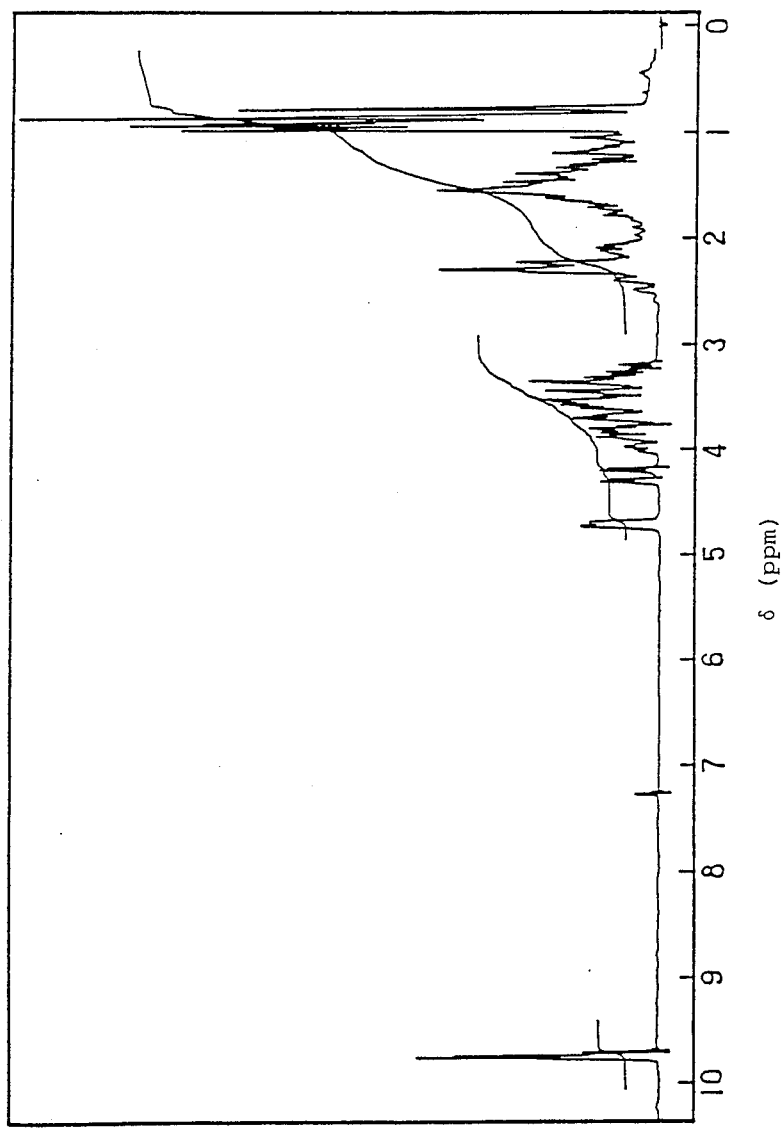
FIG. 3 shows an NMR spectrum as obtained with 5-(tetrahydro-4-methyl-2H-2-pyranoxy)-3-methylpentanal produced in accordance with the present invention.
Figure 4:
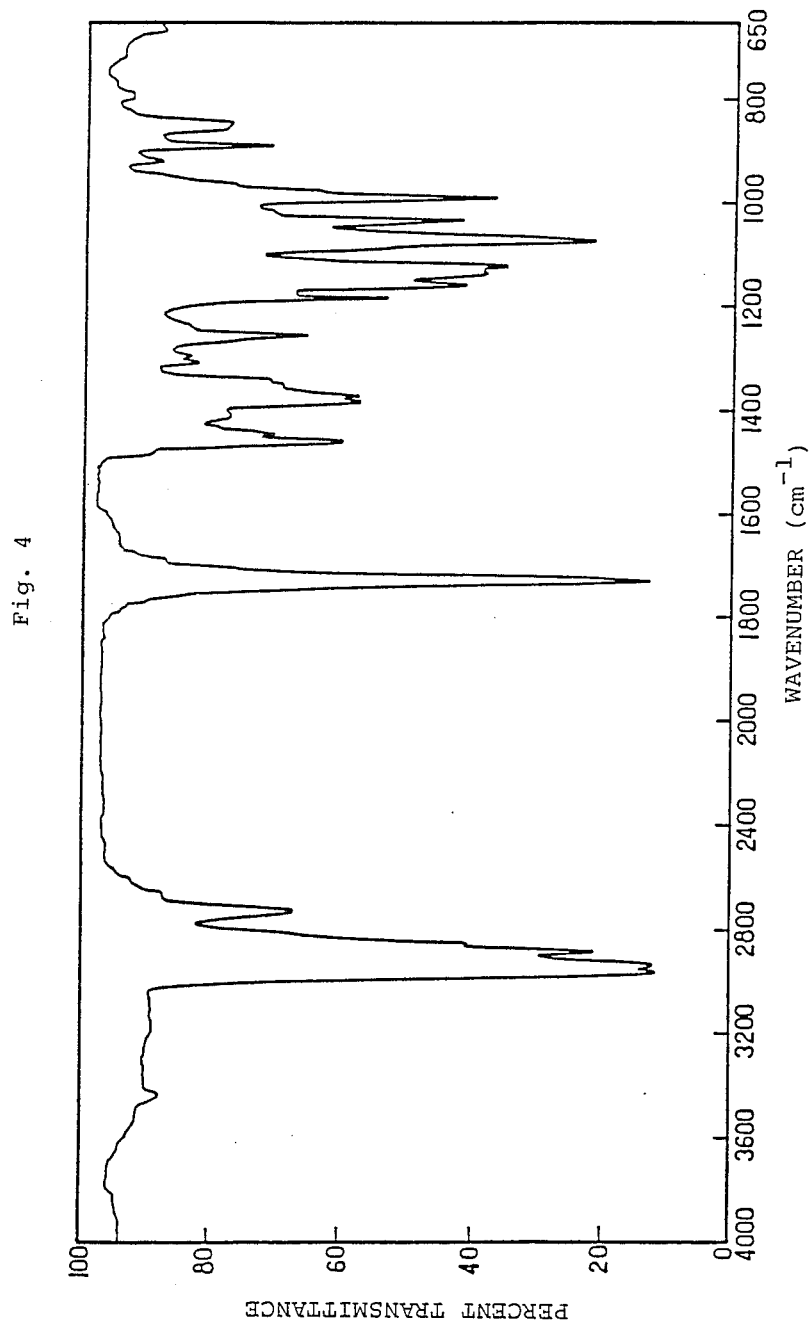
FIG. 4 is an IR spectrum as obtained with 5-(tetrahydro-4-methyl-2H-2-pyranoxy)-3-methylpentanal produced in accordance with the present invention.

A 300-ml stainless steel autoclave equipped with a magnetic stirrer was charged with 80 g of the above tetrahydro-2-(3-methyl-3-butenoxy)-4-methyl-2H-pyran, 80 ml of hexane and 0.83 mg of Rh$_4$(CO)$_{12}$. The system was purged thoroughly with a mixed gas composed of hydrogen and carbon monoxide in a mole ratio of 1:1 and, then, the pressure within the system was maintained at 200 atmospheres (absolute) with the same mixed gas. The reaction mixture was heated to 100° C. over 30 minutes with stirring and then maintained at 100° C. with stirring for 5 hours. The pressure within the system was maintained at 200 atmospheres (absolute) throughout the reaction period while the off-gas was continuously drawn out at a rate of about 5 liters/hr. After completion of the reaction, the system was returned to ordinary temperature and pressure, and the reaction mixture was taken out and analyzed by gas chromatography. The conversion of tetrahydro-2-(3-methyl-3-butenoxy)-4-methyl-2H-pyran was 99.0%. The hexane was distilled off from the hydroformylation reaction mixture and the residue was distilled under reduced pressure to give 81 g of 5-(tetrahydro-4-methyl-2H-2-pyranoxy)-3-methylpentanal as a fraction having a boiling point of 113°–114° C./4 mm Hg. A nuclear magnetic resonance (NMR) spectrum (in CDCl$_3$) and an infrared absorption spectrum (liquid film-NaCl method) each obtained with the above product are shown in FIG. 3 and FIG. 4, respectively. Field desorption ionization (FD) mass spectrometry of this product gave M$^+$ = 214.

COMPARATIVE EXAMPLE 1

Hydroformylation of tetrahydro-2-(3-methyl-3-butenoxy)-4-methyl-2H-pyran was carried out in the same manner as Example 1 except that 80 ml of toluene was used in place of hexane of Example 1 (b) and 300 mg (1.15 millimoles) of triphenylphosphine was added to the reaction system. After completion of the reaction, the system was returned to ordinary pressure, whereupon the rhodium compound in the reaction mixture did not precipitate out, hence rhodium separation by filtration was impossible. Analysis of this reaction mixture by gas chromatography indicated that the conversion of tetrahydro-2-(3-methyl-3-butenoxy)-4-methyl-2H-pyran was as low as 23% and the selectivity toward 5-(tetrahydro-4-methyl-2H-2-pyranoxy)-3-methylpentanal was 92%.

EXAMPLE 2

A 1-liter stainless autoclave equipped with a magnetic stirrer was charged with 516 g (6.00 moles) of 3-methyl-3-buten-1-ol and, as the rhodium compound, 11.7 mg (0.0625 milligram atom on the rhodium atom basis) of $Rh_4(CO)_{12}$ in an atmosphere of a carbon monoxide-hydrogen mixed gas (mole ratio=1:1), and the atmosphere within the autoclave was thoroughly substituted with a caron monoxide-hydrogen mixed gas (mole ratio=1:1). Thereafter, while maintaining the pressure within the autoclave at 200 atmospheres (absolute) with the same mixed gas, the hydroformylation reaction was conducted for 5 hours at 100° C. with stirring. Throughout the reaction period, the carbon monoxide-hydrogen mixed gas (mole ratio=1:1) was continuously fed into the autoclave through a pressure controller to maintain the pressure within the system at 200 atmospheres (absolute) while the effluent gas flow rate from the autoclave was adjusted at about 5 liters/hr. The reaction mixture was transferred with the aid of pressure to a 2-liter autoclave which had been previously purged with nitrogen gas, and the mixture was stirred at 100° C. under nitrogen gas at 20 atmospheres (absolute) for 30 minutes. After cooling and depressurizing, the metallic rhodium precipitate was filtered off from the contents obtained. In this way, 95% of the rhodium compound used was recovered in the form of metallic rhodium. The reaction mixture (675 g) after removal of the metallic rhodium precipitate was analyzed by gas chromatography. The unreacted 3-methyl-3-buten-1-ol amounted to 0.01 mole (conversion of 3-methyl-3-buten-1-ol, 99.8%) and the yield of 2-hydroxy-4-methyltetrahydropyran was 2.0 moles (selectivity based on 3-methyl-3-buten-1-ol charged, 33%). Other main products were 1.39 moles (selectivity 46.2%) of bis(tetrahydro-4-methyl-2H-2-pyranyl) ether, 0.12 mole (selectivity 4.0%) of tetrahydro-2-(3-methyl-3-butenoxy)-4-methyl-2H-pyran, 0.06 mole (selectivity 2.0%) of 5-(tetrahydro-4-methyl-2H-2-pyranoxy)-3-methylpentanal, 0.18 mole (selectivity 6.0%) of tetrahydro-2-(3-methyl-2-butenoxy)-4-methyl-2H-pyran, 0.43 mole (selectivity 7.2%) of isovaleraldehyde and 0.04 mole (selectivity 0.7%) of 3-methyl-2-buten-1-ol.

EXAMPLE 3

Hydroformylation of 3-methyl-3-buten-1-ol (516 g, 6.00 moles) was carried out in the same manner as Example 2 except that 15.4 mg (0.0624 milligram atom on the rhodium atom basis) of di-$\mu$-chlorobis(1,5-cyclooctadiene)dirhodium was used as the rhodium compound. The metallic rhodium precipitate was collected by filtration from the contents obtained, whereby 96% of the rhodium used was recovered. Analysis of the reaction mixture (670 g) by gas chromatography indicated that the mixture contained 0.04 mole (conversion of 3-methyl-3-buten-1-ol, 99.3%) of 3-methyl-3-buten-1-ol, 1.8 moles (selectivity 30%) of 2-hydroxy-4-methyltetrahydropyran, and further, 1.4 moles (selectivity 46.7%) of bis(tetrahydro-4-methyl-2H-2-pyranyl) ether, 0.12 mole (selectivity 4.0%) of tetrahydro-2-(3-methyl-3-butenoxy)-4-methyl-2H-pyran, 0.06 mole (selectivity 2.0%) of 5-(tetrahydro-4-methyl-2H-2-pyranoxy)-3-methylpentanal and 0.20 mole (selectivity 6.7%) of tetrahydro-2-(3-methyl-2-butenoxy)-4-methyl-2H-pyran.

EXAMPLE 4

Hydroformylation of 3-methyl-3-buten-1-ol (516 g, 6.00 moles) was carried out in the same manner as Example 2 except that 15 mg (0.077 milligrams atom on the rhodium atom basis) of $[Rh(CO)_2Cl]_2$ was used as the rhodium compound. The metallic rhodium precipitate was filtered off from the contents obtained, whereby 91% of the rhodium used was recovered. The reaction mixture (667 g) after filtration was analyzed by gas chromatography. Unreacted 3-methyl-3-buten-1-ol amounted to 0.01 mole (conversion 99.8%) and the yield of 2-hydroxy-4-methyltetrahydropyran was 1.7 moles (selectivity 28%). The formation of 1.38 moles (selectivity 46%) of bis(tetrahydro-4-methyl-2H-2-pyranyl) ether, 0.11 mole (selectivity 3.7%) of tetrahydro-2-(3-methyl-3-butenoxy)-4-methyl-2H-pyran, 0.07 mole (selectivity 2.3%) of 5-(tetrahydro-4-methyl-2H-2-pyranoxy)-3-methylpentanal, 0.20 mole (selectivity 6.7%) of tetrahydro-2-(3-methyl-2-butenoxy)-4-methyl-2H-pyran, 0.40 mole (selectivity 6.7%) of isovaleraldehyde and 0.03 mole (selectivity 0.5%) of 3-methyl-2-buten-1-ol, among others, was also detected.

EXAMPLE 5

Hydroformylation of 3-methyl-3-buten-1-ol (516 g, 6.00 moles) was carried out in the same manner as Example 2 except that 129 mg (0.063 milligram atom on the rhodium atom basis) of active carbon supporting 5 weight percent of metallic rhodium was used in lieu of $Rh_4(CO)_{12}$. The rhodium-on-active carbon was separated by filtration from the contents obtained and the reaction mixture was analyzed by gas chromatography. Unreacted 3-methyl-3-buten-1-ol amounted to 0.12 mole (conversion of 3-methyl-3-buten-1-ol, 98%) and the yield of 2-hydroxy-4-methyltetrahydropyran was 1.8 mole (selectivity 31%). There was also detected the formation of 1.38 moles (selectivity 46.0%) of bis(tetrahydro-4-methyl-2H-2-pyranyl) ether, 0.11 mole (selectivity 3.7%) of tetrahydro-2-(3-methyl-3-butenoxy)-4-methyl-2H-pyran, 0.07 mole (selectivity 2.3%) of 5-(tetrahydro-4-methyl-2H-2-pyranoxy)-3-methylpentanal, 0.19 mole (selectivity 6.3%) of tetrahydro-2-(3-methyl-2-butenoxy)-4-methyl-2H-pyran, 0.41 mole (selectivity 6.8%) of isovaleraldehyde and 0.05 mole (selectivity 0.8%) of 3-methyl-2-buten-1-ol.

COMPARATIVE EXAMPLE 2

Hydroformylation of 3-methyl-3-buten-1-ol was carried out in the same manner except that 0.47 g (1.8 millimoles) of triphenylphosphine was added to the reaction system. After completion of the reaction, the system was returned to ordinary pressure, whereupon the rhodium compound in the reaction mixture did not precipitate out, hence rhodium separation by filtration was impossible. Analysis of this reaction mixture by gas chromatography indicated that the conversion of 3-methyl-3-buten-1-ol was as low as 21% and the selectivity toward 2-hydroxy-4-methyltetrahydropyran was 85%.

EXAMPLE 6

A 1-liter stainless steel autoclave equipped with a magnetic stirrer was charged with 430 g of 3-methyl-3-buten-1-ol, 125 g of hexane and, as the rhodium compound, 3.4 mg (0.0182 milligram atom on the rhodium atom basis) of Rh₄(CO)₁₂ in an atmosphere of a carbon monoxide-hydrogen mixed gas (mole ratio=1:1), and the reaction mixture was heated to 110° C. over 40 minutes under stirring while maintaining the pressure within the autoclave at 200 atmospheres (absolute) with a carbon monoxide-hydrogen mixed gas (mole ratio=1:1). During the reaction period, the carbon monoxide-hydrogen mixed gas (mole ratio=1:1) was continuously fed into the autoclave through a pressure controller to maintain the pressure within the autoclave at 200 atmospheres (absolute) while the effluent gas flow rate from the autoclave was adjusted at about 5 liters/hr. After 5 hours of hydroformylation at 100° C. (autoclave inside temperature), the reaction mixture in the autoclave was transferred with the aid of pressure to a 2-liter autoclave which had previously been purged with nitrogen gas, and the mixture was stirred at 100° C. under nitrogen gas at 20 atmospheres (absolute) for 30 minutes. Thereafter, the inside temperature was lowered to room temperature and the autoclave inside was depressurized. The reaction mixture (680 g) was taken out and the rhodium precipitate was separated by filtration using a glass filter. Analysis by gas chromatography after filtration indicated that 17 g of unreacted 3-methyl-3-buten-1-ol remained in the reaction mixture (conversion of 3-methyl-3-buten-1-ol, 96%) and the yield of 2-hydroxy-4-methyltetrahydropyran was 456 g (selectivity based on 3-methyl-3-buten-1-ol converted, 82%).

COMPARATIVE EXAMPLE 3

The reaction procedure of Example 6 was followed except that 0.144 g (0.55 millimole) of triphenylphosphine was further added to the reaction system. Analysis of the reaction mixture by gas chromatography indicated that the conversion of 3-methyl-3-buten-1-ol was as low as 11%. The selectivity toward 2-hydroxy-4-methylhydropyran based on 3-methyl-3-buten-1-ol converted was 86%. In this example, the rhodium compound did not precipitate out upon depressurization after completion of the reaction.

EXAMPLES 7–16

An autoclave was charged with 3-methyl-3-buten-1-ol (430 g), one of the rhodium compounds listed in Table 1 in an amount equivalent to 0.0182 milligram atom on the rhodium atom basis and one of the organic solvents given in Table 1, and the hydroformylation was conducted in the same manner as Example 6. The results obtained are shown in Table 1.

TABLE 1

| Example | Rhodium compound | Organic solvent Name | Concentration[1] (wt. %) | Conversion of IPEA[2] (%) | Selectivity toward HMP[3] (%) |
|---|---|---|---|---|---|
| Example 7 | Rh₄(CO)₁₂ | Decane | 40 | 89 | 84 |
| Example 8 | Rh₄(CO)₁₂ | Cyclohexane | 30 | 95 | 83 |
| Example 9 | Rh₄(CO)₁₂ | Methylcyclohexane | 50 | 91 | 83 |
| Example 10 | (cyclo-C₈H₁₂RhCl)₂ | Benzene | 15 | 89 | 81 |
| Example 11 | Rh₄(CO)₁₂ | Toluene | 20 | 90 | 81 |
| Example 12 | RhCl₃·3H₂O | Methyl isobutyl ketone | 40 | 87 | 84 |
| Example 13 | Rh₄(CO)₁₂ | Diisopropyl ether | 30 | 88 | 84 |
| Example 14 | Rh₄(CO)₁₂ | Methyl acetate | 30 | 78 | 84 |
| Example 15 | Rh₄(CO)₁₂ | Hexane | 3 | 92 | 62 |
| Example 16 | Rh₄(CO)₁₂ | Ethanol | 30 | 58 | 63 |

Note
[1]The organic solvent concentration is the one in reaction mixture at the time of charging (prior to pressurization with carbon monoxide-hydrogen mixed gas).
[2]IPEA: 3-Methyl-3-buten-1-ol
[3]HMP: 2-Hydroxy-4-methyltetrahydropyran
[4]The selectivity toward HMP is based on 3-methyl-3-buten-1-ol converted.

EXAMPLE 17

The reaction procedure of Example 6 was followed except that the same autoclave as used in Example 6 was charged with 344 g of 3-methyl-3-buten-1-ol, 230 g of hexane and 3.6 mg (0.0192 milligram atom on the rhodium atom basis) of Rh₄(CO)₁₂ and the reaction under carbon monoxide-hydrogen mixed gas pressure was conducted for 4 hours, whereby 665 g of a reaction mixture was obtained. The precipitate rhodium was filtered off from this mixture. Analysis of the reaction mixture by gas chromatography indicated that the conversion of 3-methyl-3-buten-1-ol was 94% and the selectivity toward 2-hydroxy-4-methyltetrahydropyran based on 3-methyl-3-buten-1-ol converted was 86%. Distillation of this reaction mixture gave 264 g of a low-boiling fraction mainly composed of hexane. Gas chromatographic analysis of this distillate indicated that it contained 29 g of isovaleraldehyde in addition to hexane. The distillation residue was fractionated under reduced pressure (25 mm Hg) to give 59 g of a distillate (column top temperature 50°–95° C.). Gas chromatographic analysis indicated that this distillate was composed of 2 g of isovaleraldehyde, 21 g of unreacted 3-methyl-3-buten-1-ol, 12 g of 3-methyl-2-buten-1-ol and 23 g of 2-hydroxy-4-methyltetrahydropyran. At a column top temperature of 95° C., there was further obtained 332 g of a distillate, and this was 2-hydroxy-4-methyltetrahydropyran having a purity of not less than 99%. The yield of 2-hydroxy-4-methyltetrahydropyran obtained as the distillate was 81.5% based on reacted 3-methyl-3-buten-1-ol.

EXAMPLE 18

Hydroformylation of 3-methyl-3-buten-1-ol was carried out in the same manner as Example 6. Thereafter, the reaction mixture was transferred with the aid of pressure to a 2-liter autoclave equipped with a magnetic stirrer which had previously been charged with 25 g of activated carbon (GW; Kuraray Chemical Co., Ltd.), 500 g of water and 1 g of triethanolamine, and the whole mixture was stirred for 20 minutes at 2 atmospheres (absolute) under a carbon monoxide-hydrogen mixed gas (mole ratio=1:1) at 110° C. After cooling to room temperature and depressurization, the reaction mixture was then taken out from the autoclave through a filter to remove the activated carbon. The mixture obtained was composed of two layers, namely organic layer and aqueous layer, and each layer was analyzed by gas chromatography. It is found that the organic layer contained 14 g of unreacted 3-methyl-3-buten-1-ol remained and 366 g of product 2-hydroxy-4-methyltetrahydropyran. On the other hand, in the aqueous layer, 1 g of 3-methyl-3-buten-1-ol remained unreacted and there was also found 91 g of 2-hydroxy-4-methyltetrahydropyran. Measurement of the rhodium concentration in the organic layer and aqueous layer revealed that 96% of the rhodium in the rhodium compound charged into the reaction system had been removed by adsorption on the activated carbon.

EXAMPLE 19

A 1-liter stainless steel autoclave equipped with thermometer, magnetic stirrer, gas inlet, gas outlet and pressure controller and connected, via a pipe for liquid transfer with the aid of pressure, with a 2-liter glass autoclave equipped with a magnetic stirrer was charged with 500 ml of hexane, and 0.0125 millimole/liter [0.050 milligram atom (as rhodium atom)/liter] of $Rh_4(CO)_{12}$ and the system atmosphere was thoroughly substituted with a carbon monoxide-hydrogen mixed gas (mole ratio=1:1). Thereafter, while maintaining the pressure within the stainless autoclave at 150 atmospheres (absolute) with the above mixed gas, the mixture was heated with stirring until the inside temperature reached to a constant temperature of 100° C. and, then, 75 g of 3-methyl-3-buten-1-ol was continuously fed into the stainless autoclave through a constant-rate feed pump over 30 minutes. Throughout the reaction period, the same carbon monoxide-hydrogen mixed gas was fed into the autoclave so that the pressure in the autoclave was maintained at 150 atmospheres (absolute) while the rate of the effluent gas flow from the autoclave was adjusted to about 5 liters/hr. After completion of the feeding of 3-methyl-3-buten-1-ol, the reaction was still allowed to proceed with stirring under the same conditions for 2 additional hours. After 2.5 hours of reaction in total, stirring was stopped and the autoclave inside temperature was lowered quickly to around room temperature. Thereafter, the autoclave inside was depressurized to 20 atmospheres (absolute) and a trace amount of the reaction mixture was taken out from the autoclave and analyzed by gas chromatography. It was found that unreacted 3-methyl-3-buten-1-ol amounted to 1.5 g (conversion of 3-methyl-3-buten-1-ol, 98%) and the yield of 2-hydroxy-4-methyl-hydropyran was 84 g (selectivity 85%).

The 2-liter glass autoclave equipped with a magnetic stirrer and connected with the stainless steel autoclave was purged with a carbon monoxide-hydrogen mixed gas (mole ratio=1:1) and charged with 500 ml of water and, then, the above reaction mixture was transferred with the aid of pressure from the stainless steel autoclave to the glass autoclave. When the transfer was complete, the system was maintained at a pressure of 5 atmospheres (absolute) in the mixed gas atmosphere and stirred in this condition for 20 minutes for effect extraction. The extraction temperature was 30° C. Upon termination of the stirring, the liquid mixture was separated into two layers. After standing for 10 minutes, the lower aqueous layer alone was taken out of the system taking advantage of the system inside pressure. Such aqueous extract layer was analyzed by gas chromatography. It was found that 70% of the 2-hydroxy-4-methyltetrahydropyran produced had been extracted into the aqueous layer.

The extraction residue layer in the glass autoclave was transferred with the aid of pressure back to the stainless steel autoclave, and the hydroformylation of 3-methyl-3-buten-1-ol followed by extraction was repeated under the same conditions. In this manner, said hydroformylation and extraction procedure was repeated five times in all without further addition of the rhodium compound or hexane. In the 2nd, 3rd, 4th and 5th runs of the hydroformylation of 3-methyl-3-buten-1-ol, the conversion rates were 98%, 97%, 97% and 98%, respectively, and the selectivity toward 2-hydroxy-4-methyltetrahydropyran was constantly 85%. In each extraction, the 2-hydroxy-4-methyltetrahydropyran concentration in the aqueous extract layer was in the range of 1.0-1.3 moles per liter. The dissolution of the rhodium compound into the aqueous extraction layer in the second and the subsequent extractions was slight, namely within the range of 0.03-0.05 ppm in terms of rhodium atom concentration.

EXAMPLE 20

The hydroformylation and extraction procedure of Example 19 was repeated five times except that the autoclave was charged with 500 ml of cyclohexane and 0.025 millimole/liter of $(cyclo\text{-}C_8H_{12}RhCl)_2$ and that the reaction conditions were as follows: pressure, 200 atmospheres (absolute); temperature, 120° C.; reaction time after feeding of 3-methyl-3-buten-1-ol, 1 hour (1.5 hours in total). Gas chromatographic analysis of the liquid reaction mixture after completion of the reaction indicated that the conversion of 3-methyl-3-buten-1-ol was within the range of 98-99% and the selectivity toward 2-hydroxy-4-methyltetrahydropyran was always 84%. In the second and subsequent extractions, the 2-hydroxy-4-methyltetrahydropyran concentration in the aqueous extract layer was within the range of 1.0-1.3 moles/liter and the percentage extraction of 2-hydroxy-4-methyltetrahydropyran into the aqueous layer was on the average 70%. The dissolution of the rhodium compound into the aqueous extract layer was as small as 0.05-0.08 ppm in terms of rhodium atom concentration.

EXAMPLE 21

The hydroformylation and extraction procedure of Example 19 was repeated five times except that the autoclave was charged with 100 ml of toluene and 0.025 millimole/liter of $Rh_4(CO)_{12}$, that the reaction temperature was 90° C. and that 300 ml of water was used for extraction. After completion of the reaction, the reaction mixture was analyzed by gas chromatography and it was found that the conversion of 3-methyl-3-buten-1-ol was 94-95% and the selectivity toward 2-hydroxy-4-methyltetrahydropyran was always 85%. In the second and subsequent extractions, the 2-hydroxy-4-methyltetrahydropyran concentration in the aqueous extract layer was within the range of 1.3-1.9 moles/liter and percentage extraction of 2-hydroxy-4-methyltetrahydropyran into the aqueous layer was on the average 42%. The dissolution of the rhodium compound into the aqueous extract layer was slight, namely within the range of 0.07-0.15 ppm in terms of rhodium atom concentration.

EXAMPLE 22

The hydroformylation and water extraction procedure of Example 19 was carried out (once). The conversion of 3-methyl-3-buten-1-ol in the hydroformylation was 98%, the selectivity toward 2-hydroxy-4-methyltetrahydropyran was 85%, the 2-hydroxy-4-methyltetrahydropyran concentration in the aqueous extract layer in the water extraction was 0.91 mole/liter, and the dissolution of the rhodium compound into the aqueous layer was as small as 0.05 ppm in terms of rhodium atom concentration. This aqueous solution was transferred to a 2-liter flask equipped with a stirrer and mixed with 500 ml of isopropyl acetate under stirring. The resultant mixture was allowed to stand and the upper isopropyl acetate layer was analyzed by gas chromatography. The 2-hydroxy-4-methyltetrahydropyran concentration in said isopropyl acetate solution was found to be 0.71 mole/liter.

EXAMPLES 23 TO 25

The hydroformylation, water extraction and reextraction procedure of Example 22 was repeated in the same manner except that each extractant given in Table 2 was used in lieu of the organic extractant isopropyl acetate in the reextraction step. The 2-hydroxy-4-methyltetrahydropyran concentration in the organic extractant layer after reextraction as attained is shown in Table 2.

TABLE 2

| Organic extractant | HMP[1] concentration (mole/liter) |
|---|---|
| Example 23 Methyl isobutyl ketone | 0.70 |
| Example 24 Benzene | 0.61 |
| Example 25 3-Methyl-3-buten-1-ol | 0.66 |

Note:
[1]HMP: 2-Hydroxy-4-methyltetrahydropyan.

EXAMPLE 26

The first hydroformylation and water extraction was carried out in the same manner as Example 19. After completion of the reaction, the reaction mixture was analyzed by gas chromatography and it was found that the conversion of 3-methyl-3-buten-1-ol was 98% and the selectivity toward 2-hydroxy-4-methyltetrahydropyran was 85%.

A 2-liter three-necked flask was connected with the above-mentioned 2-liter glass autoclave for water extraction, purged with nitrogen, and charged with 500 ml of isobutyl acetate. Thereafter, the aqueous extract obtained by water extraction was transferred from the glass autoclave to said flask with the aid of pressure. The extraction residue layer in the glass autoclave was transferred with the aid of pressure to the stainless steel autoclave and the hydroformylation of 3-methyl-3-buten-1-ol was again performed under the same conditions and by the same procedure, during which the isobutyl acetate and the above aqueous extract in the flask were mixed with stirring at 30° C. for 10 minutes and then allowed to stand for 10 minutes, followed by transfer, with the aid of pressure, of the lower aqueous layer to the glass autoclave and drawing out the upper isobutyl acetate layer from the system within the flask. Analysis of such isobutyl acetate solution by gas chromatography indicated that 53% of the 2-hydroxy-4-methyltetrahydropyran formed in the first hydroformylation run had been taken out of the system in the form of isobutyl acetate solution.

In this manner, the serial procedure comprising hydroformylation, water extraction and isobutyl acetate extraction was repeated to five times in all. In the hydroformylation step, the conversion of 3-methyl-3-buten-1-ol was 97–88% and the selectivity toward 2-hydroxy-4-methyl-tetrahydropyran was constantly 85%. The amounts of 2-hydroxy-4-methyltetrahydropyran taken out in the form of isobutyl acetate solution in the 2nd, 3rd, 4th and 5th extraction with isobutyl acetate were 0.58 mole, 0.66 mole, 0.71 mole and 0.74 mole, respectively.

EXAMPLE 27

A 1-liter autoclave equipped with a magnetic stirrer was charged with 500 g (3.85 moles) of 3-methyl-3-butenyl acetate and, as the rhodium compound, 10 mg (0.0534 milligram atom on the rhodium atom basis) of $Rh_4(CO)_{12}$ under the atmosphere of carbon monoxide-hydrogen mixed gas (mole ratio 1:1). The system atmosphere was thoroughly substituted with the carbon monoxide-hydrogen mixed gas (mole ratio 1:1). The hydroformylation reaction was carried out by heating the autoclave contents at 100° C. with stirring for 5 hours while maintaining the pressure within the autoclave at 180 atmospheres (absolute) with said mixed gas. During the reaction, the carbon monoxide-hydrogen mixed gas (mole ratio 1:1) was continuously fed through a pressure controller to thereby maintain the system pressure at 180 atmospheres (abolute), while the effluent gas from the autoclave was adjusted to about 5 liters/hour. Then, the reaction mixture in the autoclave was transferred with the aid of pressure to a 2-liter autoclave previously charged with 700 mg of water and 5 g of activated carbon (GA; Kuraray Chemical Co., Ltd.) and the resultant mixture was stirred at 100° C. under a carbon monoxide-hydrogen mixed gas (mole ratio 1:1) at a pressure of 5 atmospheres (absolute) for 30 minutes. After cooling and depressuring, the activated carbon was filtered off from the contents, whereby 98% of the rhodium used was adsorbed on the activated carbon and separated from the reaction mixture. Water was removed by phase separation and the organic layer obtained was distilled under reduced pressure to give 530 g of 5-acetoxy-3-methylpentanal as a fraction boiling at 71°–72° C. under 10 mm Hg (yield based on 3-methyl-3-butenyl acetate charged, 86%).

EXAMPLE 28

A 2-liter autoclave equipped with a magnetic stirrer was charged with 40 g of Raney nickel pretreated with dilute aqueous acetic acid having a pH of 4, together with 600 ml of ethanol and 500 ml of water. The solution showed a pH of 5.0. The system atmosphere was thoroughly substituted with hydrogen gas and then the autoclave contents were maintained at a constant temperature of 100° C. under stirring while maintaining the autoclave inside pressure at 50 atmospheres (absolute) with hydrogen gas. To this system, there was fed 670 g of the hydroformylation reaction mixture obtained in Example 2 continuously over 6 hors through a constant flow rate pump. Throughout the reaction period, hydrogen gas was continuously fed through a pressure controller to thereby maintain the system pressure at 50 atmospheres (absolute), while the flow rate of the effluent gas from the autoclave was adjusted at 20 liters/hour. After completion of the continuous feeding of the reaction mixture, stirring was continued for an additional hour. After cooling and depressurizing, the contents were taken out from the autoclave, and the catalyst was filtered off. The reaction mixture thus obtained had a pH of 5.2 and was analyzed by gas chromatography, which showed that 62 g of isoamyl alcohol and 622 g of 3-methylpentane-1,5-diol had been formed. The yield of 3-methylpentane-1,5-diol was 88% based on the 3-methyl-3-buten-1-ol charged into the hydroformylation reaction system in Example 2.

EXAMPLE 29

The hydrogenation reaction was carried out in the same manner as Example 28 except that the autoclave was charged with 40 g of Raney nickel together with 600 ml of ethanol and 500 ml of water, followed by adjustment of the pH of the solution to 5.0 by adding 1.5 g of acetic acid and that 670 g of hydroformylation reaction mixture obtained in Example 3 was used. After completion of the reaction, the reaction mixture had a pH of 5.1. Analysis of this reaction mixture by gas chromatography indicated the formation of 3-methylpentane-1,5-diol in a yield of 87% based on the 3-methyl-3-buten-1-ol charged into the hydroformylation reaction system in Example 3. Isoamyl alcohol was the only byproduct.

EXAMPLE 30

Hydrogenation of the reaction mixture (667 g) obtained after filtration in Example 4 was carried out in the same manner as Example 28 except that a Raney nickel catalyst pretreated with a diluted hydrochloric acid having a pH of 4 was used (pH of the solution at the time of catalyst charge, 5.0). There was obtained 613 g of 3-methyl-pentane-1,5-diol. The reaction mixture at the time of completion of the reaction had a pH of 5.1. The yield of 3-methylpentane-1,5-diol was 86% based on the 3-methyl-3-buten-1-ol charged into the hydroformylation reaction system in Example 4.

EXAMPLE 31

Hydrogenation of the hydroformyltion reaction mixture (665 g) obtained in Example 5 was carried out in the same manner as Example 28 except that the autoclave was charged with 40 g of Raney nickel, 600 ml of ethanol and 500 ml of water, followed by adjustment of the pH of the solution to 3 by adding 2.5 g of acetic acid. After completion of the reaction, the reaction mixture obtained had a pH of 3. Analysis of said mixture by gas chromatography showed the formation of 3-methylpentate-1,5-diol in a yield of 86% (based on the 3-methyl-3-buten-1-ol charged into the hydroformylation reaction system in Example 5).

EXAMPLE 32

Hydroformylation of 3-methyl-3-buten-1-ol (516 g) was carried out in the same manner as Example 3. The precipitate metallic rhodium was filtered off from the reactor contents to give 670 g of a hydroformylation product. This product was hydrogenated in the same manner as Example 28 except that the autoclave was charged with 40 g of Raney nickel and 1,100 ml of water, followed by adjustment to the pH of the solution to 4 by adding 1.8 g of acetic acid. After completion of the reaction, the reaction mixture had a pH of 4. Gas chromatographic analysis of such reaction mixture showed the formation of 3-methylpentane-1,5-diol in a yield of 84% based on the 3-methyl-3-buten-1-ol charged into the hydroformylation reaction system.

EXAMPLE 33

Hydroformylation of 3-methyl-3-buten-1-ol (516 g) was carried out in the same manner as Example 3. The precipitate metallic rhodium was filtered off from the reactor contents obtained to give 670 g of a hydroformylation product. Said hydroformylation product was hydrogenated in the same manner as Example 28 except that the autoclave was charged with 50 g of a powdery nickel-on-diatomaceous earth catalyst (nickel content 50% by weight) together with 600 ml of ethanol and 500 ml of water and that the autoclave inside temperature was raised to and maintained at 140° C. with stirring while maintaining the autoclave inside pressure at 100 atmospheres (absolute) with hydrogen gas. Analysis, after completion of the reaction, of the reaction mixture indicated the formation of 3-methylpentane-1,5-diol in a yield of 84% based on the 3-methyl-3-buten-1-ol charged into the hydroformylation reaction system.

COMPARATIVE EXAMPLE 4

Hydroformylation of 3-methyl-3-buten-1-ol (516 g) was carried out in the same manner as Example 2. The precipitate metallic rhodium was filtered off from the reactor contents obtained to give 670 g of a hydroformylation reaction mixtue. Gas chromatographic analysis showed that said reaction mixture contained 0.01 mole of unreacted 3-methyl-3-buten-1-ol (conversion of 3-methyl-3-buten-ol, 99.8%) and 2.0 moles of 2-hydroxy-4-methyltetrahydropyran (selectivity 33%).

An autoclve was charged with 40 g of Raney nickel together with 1 liter of ethanol. Thereto was fed continuously the hydroformylation reaction mixture (670 g) over 6 hours while maintaining the autoclave inside temperature at 100° C. with stirring under a hydrogen pressure of 50 atmospheres (absolute). Thereafter, the reaction was continued for further 1 hour with stirring, the contents were then taken out and the catalyst was separated by filtration. Gas chromatographic analysis of the reaction mixture obtained showed that the yield of 3-methylpnetane-1,5-diol was only 260 g (yield based on the 3-methyl-3-buten-1-ol charged into the hydroformylation reaction system, 37%).

COMPARATIVE EXAMPLE 5

Hydroformylation of 3-methyl-3-buten-1-ol (516 g) was carried out in the same manner as Example 2. The precipitate metallic rhodium was filtered off from the contents obtained. Gas chromatographic analysis showed that the thus-obtained reaction mixture (670 g) contained 0.01 mole of unreacted 3-methyl-3-buten-1-ol (conversion of 3-methyl-3-buten-1-ol, 99.8%) and 2.0 moles of 2-hydroxy-4-methyltetrahydropyran (selectivity 33%).

An autoclave was charged with 40 g of Raney nickel together with 1 liter of water. This solution has a pH of 8. Thereto was fed continuously the above hydroformylation reaction mixture (670 g) over 6 hours while maintaining the autoclave inside at a hydrogen pressure of 50 atmospheres (absolute) and a temperature of 100° C. with stirring. Thereafter, the reaction was continued for 1 hour with stirring. After cooling and depressurizing, the contents were taken out and the catalyst was separated by filtration. The reaction mixture obtained had a pH of 8. Analysis of this reaction mixture by gas chromatography showed that the yield of 3-methyl-pentane-1,5-diol was only 275 g (yield based on the 3-methyl-3-buten-1-ol charged into the hydroformylation reaction system, 39%).

EXAMPLE 34

(a) Hydroformylation of tetrahydro-2-(3-methyl-3-butenoxy)-4-methyl-2H-pyran

A 100-ml stainless steel autoclave equipped with a magnetic stirrer was charged with 30 g (0.163 mole) of tetrahydro-2-(3-methyl-3-butenoxy)-4-methyl--2H-pyran, 20 ml of hexane and 0.14 mg of $Rh_4(CO)_{12}$. The system atmosphere was thoroughly substituted with a mixed gas composed of hydrogen and carbon monoxide (hydrogen/carbon monoxide mole ratio 1/1), followed by pressurization to 250 atmospheres (absolute) with the same mixed gas. With stirring, the mixture was heated to 100° C. over 30 minutes and maintained at the same temperature for 5 hours to thereby effect the hydroformylation. Throughout the reaction period, the reactor inside pressurre was always maintained at 250 atmospheres (absolute) taking advantage of a pressure controller while the off-gas was continuously drawn out of the reaction system at a flow rate of about 5 liters/hour. After completion of the reaction, the reactor contents were cooled and depressurized to ordinary pressure, and the reaction mixture was taken out. The reaction mixture was heated to 100° C. in a nitrogen atmosphere and then cooled, and the resulting precipitate (rhodium compound) was filtered off. Removal of the hexane from the filtrate by distillation gave 34.8 g of a hydroformylation product as a distillation residue. A main component of this residue was 5-(tetrahydro-4-methyl-2H-2-pyranoxy)-3-methylpentanal.

(b) Hydrogenation of the hydroformylation product

A 300ml stainless steel autoclave equipped with a magnetic stirrer was charged with 100 ml of methanol, 50 ml of water, 10 g of the above hydroformylation product and 2 g of a powdery nickel-on-diatomaceous earth catalyst (nickel content 50% by weight). The hydroformylation product was hydrogenated at 140° C. with stirring for 2 hours while maintaining the hydrogen pressure at 50 atmospheres (absolute). After completion of the hydrogenation reaction, the reaction mixture was analyzed by gas chromatography. It was found that the conversion of the hydroformylation product was 100% and the hydrogenation product was composed of 97.0 mole percent of 3-methylpentane-1,5-diol, 2.5 mole percent of 2-isopropylpropane-1,3-diol and 0.5 mole percent of isoamyl alcohol. The catalyst was filtered off from the reaction mixture, the methanol and water were distilled off and the residue was distilled under reduced pressure to give 10.5 g of pure 3-methylpentane-1,5-diol as a fraction boiling at114° C./4 mm Hg.

(c) Production of tetrahydro-2-(3-methyl-3-butenoxy)-4-methyl-2H-pyran from the Hydroformulation Product A 100-ml three-necked flask equipped with condenser, stirrer and thermometer was charged with 10 g of the above hydroformylation product, 8.6 g (0.1 mole) of 3-methyl-3-buten-1-ol, 20 ml of hexane and 1 g of active clay, and the mixture was stirred at 65° C. for 1 hour. The reaction mixture thus obtained was analyzed by gas chromatography and it was found that the conversion of the hydroformylaton product was 100% and the yield of tetrahydro-2-(3-methyl-3-butenoxy)-4-methyl-2H-pyran was 96% based on the 3-methyl-3-buten-1-ol converted.

EXAMPLE 35

(a) Production of 2-hydroxy-4-methyltetrahydropyran

The procedure of Example 17 was repeated to give 2-hydroxy-4-methyltetrahydropyran.

(b) Simultaneous production of β-methyl-δ-valerolactone and 3-methylpentane-1,5-diol A 100-ml three-necked flask equipped with dropping funnel, condenser, stirrer and thermometer was charged with 0.5 g of a powdery (passing through a 200-mesh sieve) copper chromite catalyst (N 203; $CuO-Cr_2O_3$, 0.5% $MnO_2$; Nikki Chemical Co., Ltd.) and 25 ml of dioctyl phthalate. The flask inside was purged with a nitrogen gas atmosphere at 1 atmosphere (absolute) and then the solution was heated to 160° C. with stirring, followed by dropwise addition, at 160° C., of 25 g of the 2-hydroxy-4-methyltetrahydropyran obtained above from the dropping funnel over 10 minutes. Thereafter, the resulting mixture was stirred at 160° C. for further 50 minutes and, then, the reaction mixture was cooled. Gas chromatographic analysis of the reaction mixture obtained indicated that the conversion of 2-hydroxy-4-methyltetrahydropyran was 99%, with the formation of β-methyl-δ-valerolactone and 3-methylpentane-1,5-diol in selectivities of 57% and 43%, respectively.

EXAMPLES 36–39 AND COMPARATIVE EXAMPLES 6–7

The procedure of Example 35 (b) was repeated at a reaction temperature specified in Table 3 using a catalyst given in Table 3. The results obtained in this manner are shown in Table 3.

TABLE 3

| Example or Comparative Example | Catalyst | Reaction temperature (°C.) | Conversion of HMP[1] (%) | Selectivity (%)[2] | |
|---|---|---|---|---|---|
| | | | | MVL[3] | MPD[4] |
| Example 36 | Copper-zinc oxide[5] | 160 | 99 | 57 | 43 |
| Example 37 | Copper-chromium-zinc oxide[6] | 140 | 91 | 58 | 42 |
| Example 38 | Copper chromite[7] | 180 | 100 | 59 | 41 |
| Example 39 | Copper chromite[7] | 120 | 82 | 56 | 44 |
| Comparative Example 6 | Copper chromite[7] | 210 | 100 | 94 | 6 |
| Comparative | Copper chromite[7] | 100 | 19 | 57 | 43 |

TABLE 3-continued

| Example or Comparative Example | Catalyst | Reaction temperature (°C.) | Conversion of HMP[1] (%) | Selectivity (%)[2] | |
|---|---|---|---|---|---|
| | | | | MVL[3] | MPD[4] |
| Example 7 | | | | | |

Notes:
[1]HMP: 2-hydroxy-4-methyltetrahydropyran
[2]Selectivity toward β-methyl-δ-valerolactone or 3-methylpentane-1,5-diol based on 2-hydroxy-4-methyltetrahydropyran converted.
[3]MVL: β-methyl-δ-valerolactone
[4]MPD: 3-methylpentane-1,5-diol
[5]CuO—ZnO; Catalyst N 211 (Nikki Chemical Co., Ltd.) pulverized to enable passage through a 200-mesh sieve.
[6]CuO—Cr$_2$O$_3$—ZnO; Catalyst C-44 (Catalysts & Chemicals Inc., Far East) pulverized to enable passage through a 200-mesh sieve.
[7]CuO—Cr$_2$O$_3$, 0.5% MnO$_2$; Catalyst N 203 (Nikki Chemical Co., Ltd.)

EXAMPLE 40

(a) Production of 2-hydroxy-4-methyltetrahydropyran

The procedure of Example 17 was repeated to give 2-hydroxy-4-methyltetrahydropyran.

(b) Simultaneous production of β-methyl-δ-valerolactone and 3-methylpentane-1,5-diol A 100-ml stainless steel autoclave equipped with raw material inlet, gas inlet and magnetic stirrer was charged with 0.5 g of a powdery (passing through a 200-mesh sieve) copper chromiate catalyst (N 203; CuO-Cr$_2$O$_3$, 0.5% MnO$_2$; Nikki Chemical Co., Ltd.) 50 g of triethylene glycol dimethyl ether and 10 g of the 2-hydroxy-4-methyltetrahydropyran obtained above. The autoclave inside was pressurized to 10 atmospheres (absolute) with hydrogen gas. The mixture was heated to 140° C. over 15 minutes with vigorous stirring and then stirring was continued at that temperature for further 60 minutes. Throughout the reaction period, the pressure always maintained at 10 atmospheres (absolute) while adjusting such that the hydrogen gas flowed out as the off-gas at a rate of 10 liters/hour. After completion of the reaction, the autoclave inside was returned to ordinary temperature and pressure, and the reaction mixture was taken out. Analysis of this mixture by gas chromatography showed that the conversion of 2-hydroxy-4-methyltetrahydropyran was 98.5%, with the formation of β-methyl-δ-valerolactone and 3-methypentane-1,5-diol in selectivities of 46% and 54%, respectively.

EXAMPLE 41-44

The procedure of Example 40 (b) was repeated at a reaction pressure and reaction temperature each given in Table 4. The results obtained are shown in Table 4.

TABLE 4

| Example | Reaction pressure [atmospheres (absolute)] | Reaction temperature (°C.) | Conversion of HMP[1] (%) | Selectivity (%)[2] | |
|---|---|---|---|---|---|
| | | | | MVL[3] | MPD[4] |
| Example 41 | 17 | 140 | 96 | 40 | 60 |
| Example 42 | 6 | 180 | 99 | 49 | 51 |
| Example 43 | 11 | 130 | 88 | 44 | 56 |
| Example 44 | 31 | 180 | 99 | 17 | 83 |

Notes:
[1]HMP: 2-hydroxy-4-methyltetrahydropyran
[2]Selectivity toward β-methyl-δ-valerolactone or 3-methylpentane-1,5-diol based on 2-hydroxy-4-methyltetrahydropyran converted.
[3]MVL: β-methyl-δ-valerolactone
[4]MPD: 3-methylpentane-1,5-diol

What is claimed is:

1. A method of producing 3-methylpentane-1,5-diol which comprises reacting a compound of the general formula

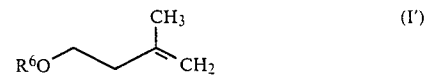

(I')

wherein R$^6$ is a hydrogen atom or a tetrahydro-4-methyl-2H-2-pyranyl group, with carbon monoxide and hydrogen in the presence of a rhodium compound free from modification by a ligand containing an element belonging to the group V of the periodic table and hydrogenating the hydroformylation product obtained in the presence of water, a hydrogenation catalyst and an acidic substance.

2. The method of claim 1, wherein the compound of general formula (I') is tetrahydro-2-(3-methyl-3-butenoxy)-4-methyl-2H-pyran and wherein part of the hydroformylation product obtained is reacted with 3-methyl-3-buten-1-ol in the presence of an acid catalyst to thereby convert the same to tetrahydro-2-(3-methyl-3-butenoxy)-4-methyl-2H-pyran and the latter is used as the raw material in the hydroformylation reaction.

3. The method of claim 1, wherein the amount of water is not less than about 0.05 parts by weight per part by weight of the hydroformylation product.

4. The method of claim 1, wherein said acidic substance is an organic acid.

* * * * *